(12) United States Patent
Shusterman

(10) Patent No.: US 10,842,440 B2
(45) Date of Patent: Nov. 24, 2020

(54) SYSTEM AND METHOD FOR MONITORING AND WIRELESSLY TRANSMITTING HEALTH DATA

(71) Applicant: Vladimir Shusterman, Pittsburgh, PA (US)

(72) Inventor: Vladimir Shusterman, Pittsburgh, PA (US)

( * ) Notice: Subject to any disclaimer, the term of this patent is extended or adjusted under 35 U.S.C. 154(b) by 658 days.

(21) Appl. No.: 15/442,705

(22) Filed: Feb. 27, 2017

(65) Prior Publication Data

US 2017/0164901 A1    Jun. 15, 2017

Related U.S. Application Data

(63) Continuation-in-part of application No. 14/470,923, filed on Aug. 27, 2014, now Pat. No. 9,610,016.

(51) Int. Cl.
```
A61B 5/02       (2006.01)
A61B 5/00       (2006.01)
G08C 17/02      (2006.01)
A61B 5/0402     (2006.01)
A61B 5/055      (2006.01)
A61B 5/0205     (2006.01)
A61B 5/026      (2006.01)
A61B 5/0488     (2006.01)
A61B 5/021      (2006.01)
A61B 5/1455     (2006.01)
A61B 5/0476     (2006.01)
A61B 5/053      (2006.01)
```
(52) U.S. Cl.
CPC ............ *A61B 5/7203* (2013.01); *A61B 5/002* (2013.01); *A61B 5/0006* (2013.01); *A61B 5/0024* (2013.01); *A61B 5/0205* (2013.01); *A61B 5/0402* (2013.01); *A61B 5/055* (2013.01); *A61B 5/7221* (2013.01); *A61B 5/7225* (2013.01); *G08C 17/02* (2013.01); *A61B 5/021* (2013.01); *A61B 5/0263* (2013.01); *A61B 5/0476* (2013.01); *A61B 5/0488* (2013.01); *A61B 5/053* (2013.01); *A61B 5/0555* (2013.01); *A61B 5/14551* (2013.01); *A61B 5/7282* (2013.01)

(58) Field of Classification Search
None
See application file for complete search history.

(56) References Cited

U.S. PATENT DOCUMENTS

| 5,730,146 A * | 3/1998 | Itil ...................... A61B 5/0476 600/545 |
| 6,221,011 B1 * | 4/2001 | Bardy .................... G16H 10/60 600/300 |
| 6,753,783 B2 * | 6/2004 | Friedman ............. A61B 5/0002 324/207.11 |

(Continued)

*Primary Examiner* — Sunit Pandya

(57) ABSTRACT

A wireless monitoring system that provides reliable wireless data transmission during patient table (bed) movement. The system makes use of at least one wireless antenna linked to the patient table to provide substantially continuous, unobstructed communication regardless of the patient table's position and the movement of medical personnel around the table. The system also utilizes adaptive filtering of electromagnetic interference, signal conditioning, and detection of cardiac-activity waveforms, providing means for adjusting signal-processing parameters to the specific features of electromagnetic interference and cardiac waveforms.

16 Claims, 23 Drawing Sheets

(56) References Cited

U.S. PATENT DOCUMENTS

| | | | | |
|---|---|---|---|---|
| 7,508,307 | B2* | 3/2009 | Albert | G08B 1/08 |
| | | | | 340/506 |
| 8,388,530 | B2* | 3/2013 | Shusterman | G16H 50/20 |
| | | | | 600/300 |
| 8,437,843 | B1* | 5/2013 | Kayyali | A61B 5/0476 |
| | | | | 600/301 |
| 8,781,563 | B2* | 7/2014 | Foo | A61B 5/1113 |
| | | | | 600/509 |
| 9,183,351 | B2* | 11/2015 | Shusterman | G06F 19/3418 |
| 2005/0165323 | A1* | 7/2005 | Montgomery | A61B 5/0006 |
| | | | | 600/544 |
| 2006/0183980 | A1* | 8/2006 | Yang | A61B 5/0022 |
| | | | | 600/301 |
| 2007/0010721 | A1* | 1/2007 | Chen | A61B 5/0002 |
| | | | | 600/300 |
| 2007/0288265 | A1* | 12/2007 | Quinian | G06F 19/3418 |
| | | | | 705/2 |
| 2011/0004110 | A1* | 1/2011 | Shusterman | G16H 50/20 |
| | | | | 600/509 |
| 2013/0172691 | A1* | 7/2013 | Tran | A61B 8/488 |
| | | | | 600/301 |
| 2013/0231947 | A1* | 9/2013 | Shusterman | G06F 19/3418 |
| | | | | 705/2 |
| 2014/0081100 | A1* | 3/2014 | Muhsin | A61B 5/0002 |
| | | | | 600/324 |
| 2014/0213872 | A1* | 7/2014 | Rahman | G06F 1/08 |
| | | | | 600/372 |
| 2014/0266776 | A1* | 9/2014 | Miller | A61B 5/14865 |
| | | | | 340/870.01 |
| 2015/0106020 | A1* | 4/2015 | Chung | G16H 50/30 |
| | | | | 702/19 |

* cited by examiner

ECG signals during real-time MRI scanning (2d SSFP sequence). EMI filtering OFF

ECG signals during real-time MRI scanning (2d SSFP sequence). EMI filtering ON

SYSTEM AND METHOD FOR MONITORING AND WIRELESSLY TRANSMITTING HEALTH DATA

STATEMENT REGARDING FEDERALLY SPONSORED RESEARCH OR DEVELOPMENT

This invention was made with government support under the contract HHSN268201400021C awarded by the National Institutes of Health. The government has certain rights in the invention.

FIELD OF THE INVENTION

This invention relates to the field of wireless biomedical devices and healthcare information management systems; and more specifically, to wireless monitoring of medical and health data (e.g., vital signs, electrocardiogram, blood pressure, pulse oximetry, electroencephalogram) in the setting of magnetic resonance imaging, X-ray guided cardiovascular procedures and other sources of electromagnetic interference.

BACKGROUND OF THE INVENTION

This application is a continuation-in-part of pending U.S. patent application Ser. No. 14/470,923 filed on Aug. 27, 2014, which is incorporated herein by reference.

The following acronyms are used in this specification:

| | |
|---|---|
| ECG—electrocardiogram/ electrocardiographic | SSFP—steady state free-precession |
| EEG—electroencephalogram | MHE—magneto-hydrodynamic effect |
| EMG—electromyogram | SVD—singular value decomposition |
| MR—magnetic resonance | GMF—gradient magnetic field |
| ABP—arterial blood pressure | EMI—electromagnetic interference |
| A/D—analog-to-digital | EMC—electromagnetic compatibility |
| DSP—digital signal processing | |
| CMR—cardiovascular magnetic resonance | |

Physiological monitoring has become an essential part of health and disease management. A number of monitoring modalities, sensors and systems have been developed for various settings and patient groups. They include in-hospital monitoring systems (e.g., bedside monitors and systems for patient monitoring during surgeries and other medical procedures), as well as out-of-hospital (ambulatory) and home monitoring systems. The most common types of collected information are ECG, EEG, EMG, temperature, respiration (breathing) rate and amplitude, oxygen saturation (pulse oximetry), ABP, glucose, hemoglobin, physical activity, vascular resistance and cardiac output.

Majority of in-hospital monitoring systems collect data from multiple sensors and/or channels. For example, cardiovascular hemodynamic monitoring often include 12-lead ECG, 4 blood-pressure and pulse-oximetry channels; the cardiac electrophysiological monitoring systems include at least 8 surface ECG channels and additional channels for collecting intracardiac electrograms, whereas the EEG monitoring systems may incorporate up to 100 channels.

Because most physiological signals are relatively small, require frequent data sampling and real-time data transmission, both electromagnetic interference and wireless data transmission represent major challenges for the development of such monitoring systems, as detailed below.

I. Electromagnetic Interference

Powerful sources of electromagnetic interference that are usually present in a modern hospital environment can generate substantial amount of noise, distortion and interference. Magnetic-resonance (MR) scanners is an example of a powerful source of electromagnetic interference, which can lead to signal artifacts that are several-orders of magnitude greater than ECG or EEG signals. This interference becomes particularly important due to the requirement for high-fidelity, diagnostic ECG monitoring during interventional cardiovascular MR procedures and tracking subtle changes in the amplitude of ECG ST-segment and T-wave, which may signal the earliest signs of ischemia in patients with coronary artery disease. Moreover, the interventional cardiovascular MR procedures also require fast patient transportation (with continuous monitoring) from the MR-scanner room to and X-ray room and back. Due to the requirement of continuous monitoring during both procedures, as well during transportation between the two rooms, a single, wireless system must be used for this setting. The frequency of the signals generated by MR-scanner's gradient magnetic fields ("GMF-interference") often overlaps with the frequency of cardiac signals ("true ECG"). In this situation, ECG signals represent a combination of the true ECG and GMF-interference. Because the magnitude of MR-gradients (GMF) is usually several orders of magnitude greater than the magnitude of the true ECG; the MR-contaminated signals require substantial filtering, which modifies the pattern of the cardiac signals and diminishes its diagnostic value. In addition, the patterns of ECG signals in the presence of strong magnetic fields are changed by the magneto-hydrodynamic effect [MHE], which arises due to the circulation of magnetized blood in subject's body. Although a number of filtering and reconstruction approaches have been developed to address this issue, an accurate, high-fidelity reconstruction of the diagnostic quality true-ECG signal remains an open challenge. (Wu V. et. al. J Adaptive Noise Cancellation to Suppress Electrocardiography Artifacts During Real-time interventional MRI. Magnetic Resonance Imaging, 33(5):1184-93. (2011).

The prior-art ECG reconstruction methods can be divided into three groups:
A. Approaches utilizing MR-gradient signals, which are either obtained directly from the MR-scanner or its control equipment, Odille et al. Noise Cancellation Signal Processing Method and Computer System for Improved Real-time Electrocardiogram Artifact Correction During MRI data Acquisition, IEEE Trans Biomed Eng, 54(4) pp. 630-40 (2007); additional "blanking" can be employed for preventing saturation of ECG amplifiers during the time periods of changes in MR-gradients, which induce large voltages in the ECG sensing cascades; Tse et al. A 1.5T MRI-Conditional 12-Lead Electrocardiogram for MRI and Intra-MR Intervention; Magnetic Resonance in Medicine 71 pp 1336-1347 (2014);
B. Methods utilizing dedicated, external antennas (coils, loops) for detecting changes in electromagnetic fields induced by MR-gradients (Laudon et al. Minimizing interference from magnetic resonance imagers during electrocardiography. IEEE Trans Biomed Eng., 45(2) pp 160-4 (1998); Felblinger et al. Restoration of Electrophysiological Signals Distorted by Inductive Effects of Magnetic Field Gradients During MR Sequences, Magnetic Resonance in Medicine, 41 pp 715-21 (1999); and
C. Approaches based on modeling ECG signals, using the signals obtained outside the MR-scanner, and relying on a simplified assumption that the ECG waveforms do not change during subsequent MR-scanning (Oster J, et. al. Nonlinear Bayesian Filtering for Denoising of Electrocardiograms Acquired in a Magnetic Resonance Environment IEEE Transactions on Biomedical Engineering. Vol. 57 No. 7, pp 1628-38 (July 2010).

II. Wireless Communication

Wireless connectivity offers mobility and convenience, which cannot be achieved using "wire-based" systems. In a hospital setting, this allows uninterrupted patient monitoring and movement of patients between different procedure/surgery rooms, intensive care units, emergency rooms and hospital beds. In an out-of-hospital or home setting, wireless systems allow continuous monitoring during sleep and daily activities; they can also be used on the road and in other settings.

However, wireless data transmission poses several challenges compared with the wire-based systems. First, the speed and rate of wireless data transmission are limited. This creates significant problems for the development of multi-channel/multi-sensor wireless systems, which require significant data throughput (such as cardiac electrophysiological systems, cardiac hemodynamic monitoring or EEG-mapping systems). Furthermore, wireless systems are susceptible to electromagnetic noise and interference from external sources. This issue is particularly important for medical monitoring in the emergency setting and during interventional procedures, where uninterrupted, high-fidelity, real-time data are essential for patient diagnosis and management. Rapid proliferation of medical equipment with powerful electromagnetic sources (e.g., magnetic-resonance (MR) scanners, X-ray machines, etc.) makes this issue particularly challenging in the modern hospital environment. Practically, this leads to the necessity to change the patient monitoring systems when a patient is moved for different diagnostic procedures and treatment throughout a hospital. This requires detachment and re-attachment of multiple ECG leads and other sensors to the patient, adding burden of time, effort and cost for medical institutions and creating discontinuities (gaps) in patient monitoring.

Traditionally, wireless radio-frequency transmitters have been viewed as a simple replacement for wire-based data transmission. Therefore, the wireless system designs have essentially copied the wire-based systems and added a single radio-frequency transmitter/receiver (Bluetooth, WiFi, Zigbee, cell-phone, etc.). However, as explained above, this design strategy can lead to several problems. Specifically, a single radio-frequency transmitter has a limited data throughput, which may not be sufficient for multi-channel, high-sampling-rate data monitoring. Furthermore, wireless communication, using a single transmitter, can be significantly affected or completely interrupted by external electromagnetic interference, which may seriously complicate patient management and outcomes in the emergency settings. Any transmission errors, delay or interruptions in this situation may be life-threatening and lead to delayed or inappropriate medical response. This problem becomes even more difficult when the distance between the wireless radio transmitter and receiver changes during the transmission (for example, when the patient is being transported between two different procedure rooms, while the data are being transmitted wirelessly to a "control room" where physicians/nurses monitor the data in real time).

SUMMARY OF THE INVENTION

This invention provides a way to use a single system for patient monitoring during various interventional procedures (including X-ray and MR-guided procedures), eliminating the need for multiple detachments/re-attachments of various monitoring systems when patient is moved from one room/procedure to another. In particular, the system of present invention enables high-fidelity, wireless, multisensor monitoring in diagnostic suites (e.g., interventional cardiology suite), treatment units (e.g., intensive care unit), as well as during patient transportation between different procedures, units, hospitals and clinics. To achieve reliable, real-time transmission of large volumes of data, the invention employs at least one and preferably at least two wireless transmitters.

As explained above, powerful electromagnetic interference generated by the MR-imaging systems contaminates physiological signals and generates the need for data filtering. In particular, filtering is required to remove GMF-interference, whose frequency spectrum often overlaps with that of the ECG signals and whose magnitude is several-fold higher than that of the ECG signals.

Because the system of present invention is mobile and wireless, it does not have any physical connections with the MR-scanner or its control equipment, which are commonly used as a source of information about MR-gradients. Instead, the system of this invention utilizes the electrodes, associated cables/electronic circuitry, and body of a monitored subject as a receiving antenna and circuitry for detecting, filtering and analyzing features and patterns of electromagnetic interference. In particular, the system of present invention separates GMF-interference from physiological signals, using a priori information (criteria) about differences of these signals' characteristics. These include differences in time-domain features (e.g., amplitude, derivatives, area, integral and waveform patterns) and frequency-domain features (dominant frequency and frequency range). The criteria are adjusted using the measurements performed at different distances from the magnet (i.e., at different strengths of magnetic field) in the presence and/or absence of working MR-gradients, as detailed in the Description of the Preferred Embodiments.

The system of present invention also reconstructs physiological signals in the presence of strong MHE, using the measurements performed at different distances from the magnet (i.e., at different strengths of magnetic field), and changes in blood flow and blood pressure, which affect the magnitude of MHE.

To summarize, the system of present invention includes the following innovative features:

I. Multiple filterbanks (filtering procedures) for recording both diagnostic-quality (broad-band) signals in the absence of EMI and filtered-out (narrow-band) signals in the presence of EMI, with subsequent reconstruction of diagnostic-quality signals from the filter-out signals using the transfer matrices (reconstruction coefficients) obtained and/or fine-tuned at the initial (calibration) stages of data recording.

II. Filtering of EMI (in particular, GMF-interference), using a priori information (criteria) about differences between the GMF and physiological signals' characteristics. The criteria are adjusted using the measurements performed at different distances from the magnet (i.e., at different strengths of magnetic field) in the presence and/or absence of working MR-gradients, III. Filtering of the magneto-hydrodynamic effect, using the physiological measurements at different distances from the magnet (i.e., at different strengths of magnetic field), and changes in blood flow and blood pressure, which affect the magnitude of MHE.

IV. At least one and preferably multiple wireless transmitters for increasing reliability and speed (throughput) of the wireless data transmission, which is critically important for large volumes of continuous, multichannel data.

One important aspect of this invention is mounting (linking/connecting) a wireless antenna to a movable/wheeled patient table (herein, the terms patient table, bed, and procedure table are used interchangeably) to enable reliable wireless data transmission at different locations of the patient table and during its movement in the course of various procedures, as well as between different procedures and/or rooms. An important aspect of this invention is the positioning of at least one antenna connected to a wireless transmitter and at least one antenna connected to a wireless receiver (herein referred to as the first and second antenna, respectively) to provide a free (unobstructed) plane (space) for substantially continuous wireless communication between the two antennas at various positions of the patient table and during table movement.

The wireless system of this invention, which provides monitoring of health data of an individual lying on a movable/wheeled patient table, includes:

at least one acquisition module with at least one sensor adapted to be placed on an individual's skin for collecting at least one physiological signal by substantially continuous monitoring of said individual's health data, and at least one wireless transmitter for substantially continuous transmission of said at least one physiological signal; and at least one wireless transmitter having at least one first antenna linked to said patient table to receive said at least one physiological signal from said acquisition module and transmitting said signal substantially continuously from various locations and during movement of the patient table and said individual;

wherein said at least one first antenna is positioned to provide substantially unobstructed communication to at least one second antenna on a receiver regardless of the location of said patient table and the movement of medical personnel around said table.

An important aspect of this invention is adapting digital signal processing (DSP) operations based on the properties of EMI and cardiac-activity waveforms as described below.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Signal Filtering and Reconstruction in the Presence of Electromagnetic Interference The system of the present invention utilizes at least one of the following approaches implemented using DSP and/or analog electronics:

I. MR-Gradient Detector

Figure 2:
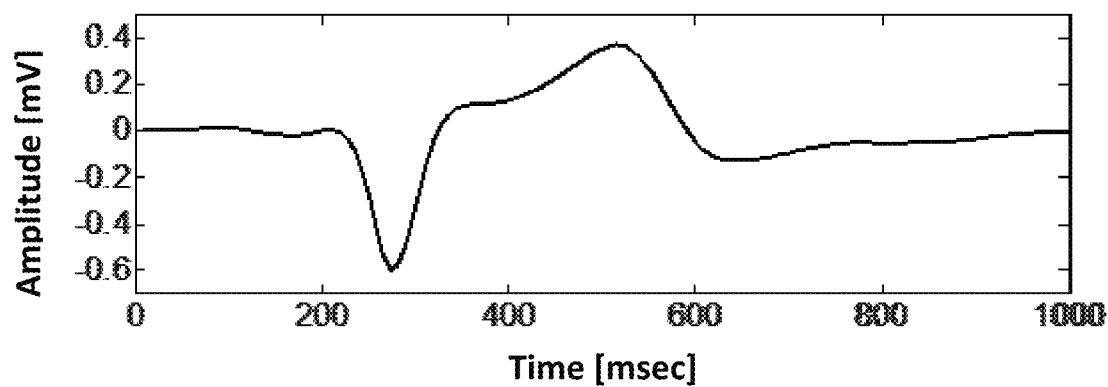
FIG. 2 is an example of an ECG signal (Lead II) recorded in a human subject outside an MR-scanner.
Figure 3:
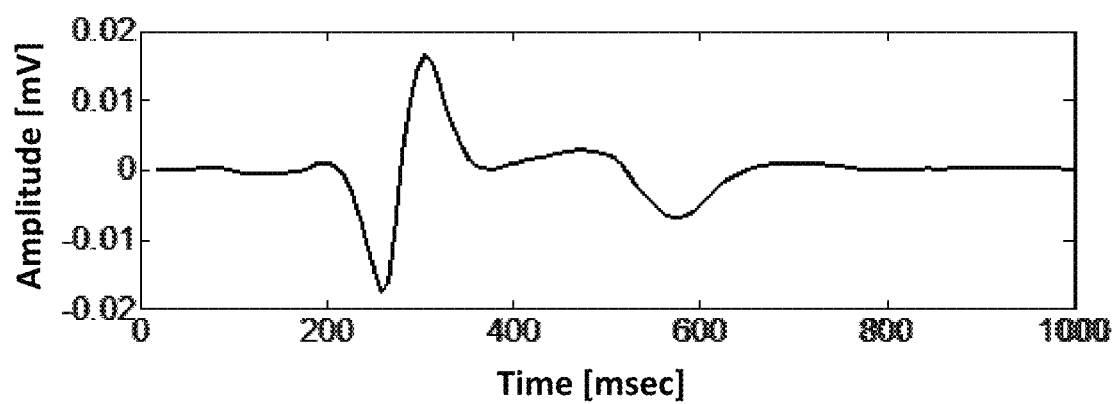
FIG. 3 is the time derivative of the ECG signal in FIG. 2.

In most pulse sequences employed in modern MR-scans, MR-gradients generate voltages with magnitudes and derivatives, which are substantially higher than those of electrophysiological signals (e.g., ECG, EEG, EMG). FIGS. 2 and 3 shows an example of an ECG signal and its time derivative, respectively; the ECG was recorded in a human subject before an MM-scan. The ECG signal has the maximum range of, approximately, 1 mV and the range of the derivative is, approximately, 0.04 mV/ms.

Figure 4:
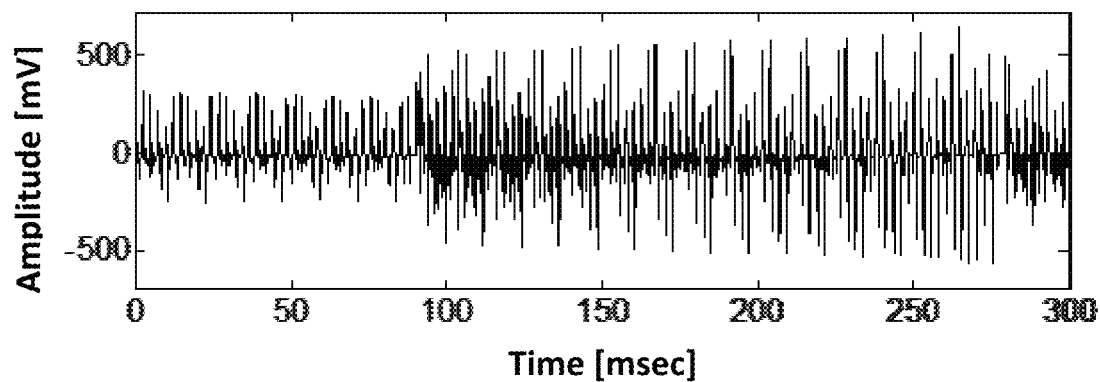
FIG. 4 is an example of GMF-interference in electrophysiological recordings obtained during a short-TE/TR pulse sequence, which is commonly used in the interventional cardiovascular MRI. The raw, unamplified signal was recorded using surface ECG electrodes, which were attached to a precordial chest region (corresponding to the ECG lead II position).
Figure 5:
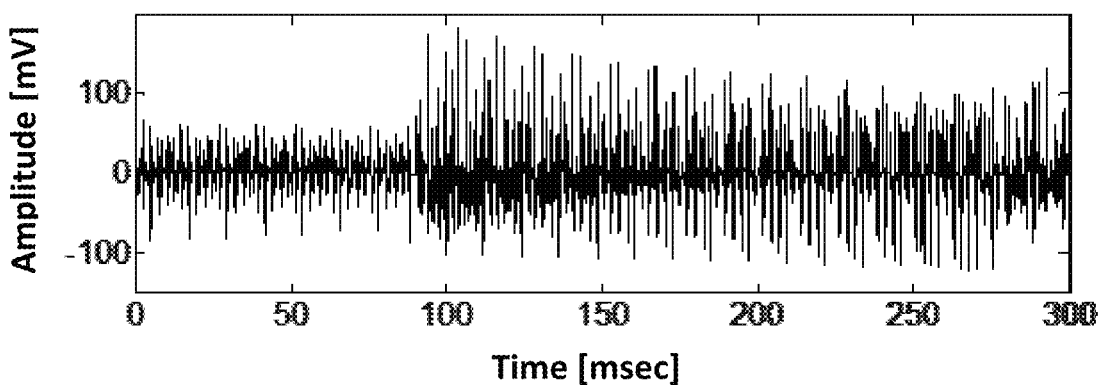
FIG. 5 is the time derivative of the GMF-interference signal in FIG. 4.

FIG. 4 shows an example of GMF-interference in electrophysiological recordings obtained during a short-TE/TR pulse sequence, which is commonly used in the interventional cardiovascular MM. The signal was recorded using surface ECG electrodes, which were attached to a precordial chest region (corresponding to the ECG lead II position). FIG. 5 shows the time derivative of the GMF-interference signal in FIG. 4. Because the magnitude of GMF and its time derivative are several orders of magnitude greater than those of ECG signals, its magnitude and time-derivative are used by the GMF-detector to discriminate between the GMF and physiological (e.g, ECG, EEG, EMG) signals. The threshold values can be set constant or adapted (adjusted, fine-tuned, optimized) automatically or manually, using the ECG signals obtained before the MR-scan. In addition, the dominant frequency of the GMF-signals (≥80 Hz) is usually higher than the dominant frequency of the ECG signals (approximately, 30-60 Hz). Equivalently, the rise-time of the GMF-signals is shorter than that for the ECG signals. Therefore, in different configurations of a method of this invention, the GMF-detector also utilizes signal's dominant frequency, rise-time, absolute magnitude (range) and/or its time derivatives (e.g., $1^{st}$ and $2^{nd}$ derivatives), waveform pattern, as well as other signal characteristics.

II. Filtering GMF Using Parallel Filterbanks

The system of present invention employs at least two banks of filters (Filterbanks) or DSP filtering procedures, which are selected using a mechanical, electronic or software-controlled (programmable) switch. Filterbank I allows recording of the "gold-standard", diagnostic quality physiological signals, using the settings specified in the appropriate performance standards (e.g., diagnostic ECG signals using a frequency band of 0.05-250 Hz, as specified in the ANSI/AAMI EC11:1991/(R)2007 "Diagnostic electrocardiographic devices"). However, Filterbank I cannot effectively filter out GMF-interference, which often overlaps with the spectrum of the ECG signals, and Filterbank II is designed for filtering out the GMF (e.g., using a low-pass, 8-th order Butterworth filter with a 40-Hz 3 dB cutoff frequency). Filterbank II, however, does not provide the bandwidth required for the diagnostic ECG evaluation of the cardiac waveforms (e.g., changes in the ST-segment and T-wave).

Block-diagrams of several configurations of a medical device of this invention with different types of arrangement of the Filterbanks and GMF-detector are shown in FIG. 6-10.

The switchable Fiterbanks allow clinicians to use a single monitoring system for various procedures with different levels of electromagnetic interference (EMI). For example, Filterbank I can be used to obtain diagnostic ECG in the environments with relatively low levels of EMI, for example, during the course of X-ray guided cardiovascular procedures, patient transportation, as well as bed-side monitoring. Switching from Filterbank I to Filterbank II allows uninterrupted data monitoring in the environments with a high level of EMI, such as MR-imaging.

In addition, switchable Filterbanks are useful for efficient filtering and reconstruction of physiological signals, as described below.

III. Filtering GMF Using Time-Domain GMF Features

Because GMF-interference is several-orders-of-magnitude greater than the cardiac electrical activity, it may cause saturation of amplifiers and/or filters in the monitoring systems' electronic circuitry.

The utility of frequency-domain filtering of GMF-interference is limited by an overlap between the frequency ranges of physiological signals (e.g., ECG has a frequency range of 0.05-250 Hz) and GMF-interference (80-1000 Hz). In addition, the amplitude and derivative of GMF-signal is several orders of magnitude greater than those for physiological signals, and with respect to the low-amplitude/derivative physiological signals, it can be approximated by Dirac delta or Heaviside step function (the integral of the delta function). The frequency power spectrum of the delta function has a constant amplitude and broad distribution (spans all frequencies). Therefore, time-domain approaches implemented in DSP and/or analog electronics are beneficial for filtering GMF-signals, as shown below. They include bitwise operations combined with voltage division and/or multiplication, pattern recognition, template matching and wavelet-based filtering tailored to characteristics and/or patterns of the GMF-signals.

Figure 11:
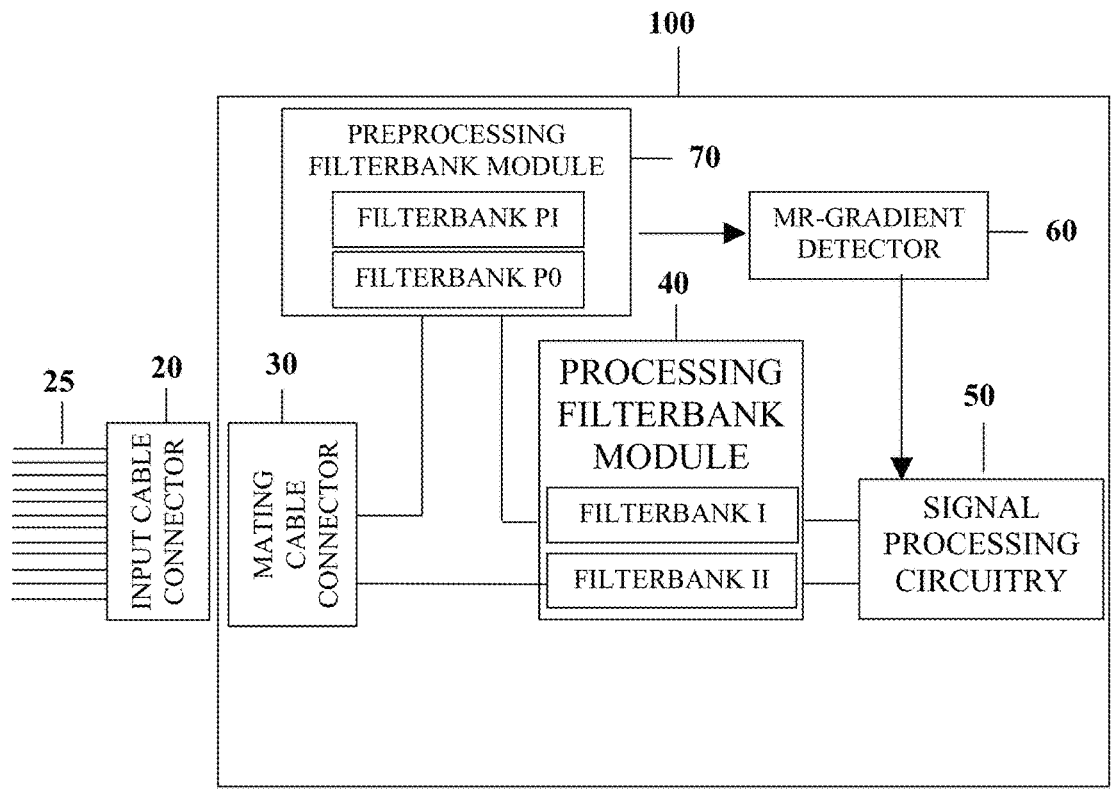
FIG. 11 is a block-diagram of the system configuration, which includes a Preprocessing Filterbank Module (70) with Filterbank P1 and Filterbank P0.
Figure 12:
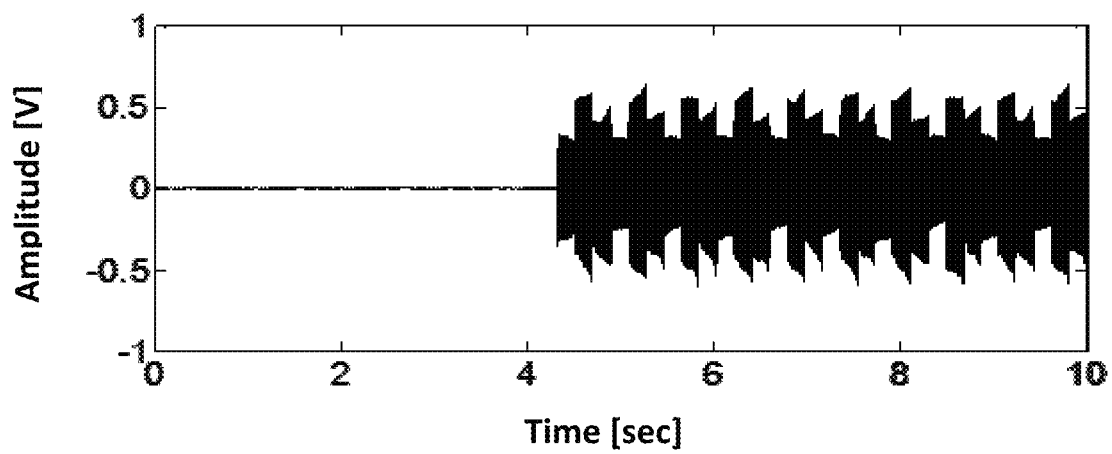
FIG. 12 is an example of a raw (unamplified and unfiltered) signal that was recorded using surface ECG electrodes (corresponding to the ECG lead II). The MR-scanning was initiated, approximately, 4 sec after the beginning of the recording and was associated with a large-amplitude GMF-interference.
Figure 13:
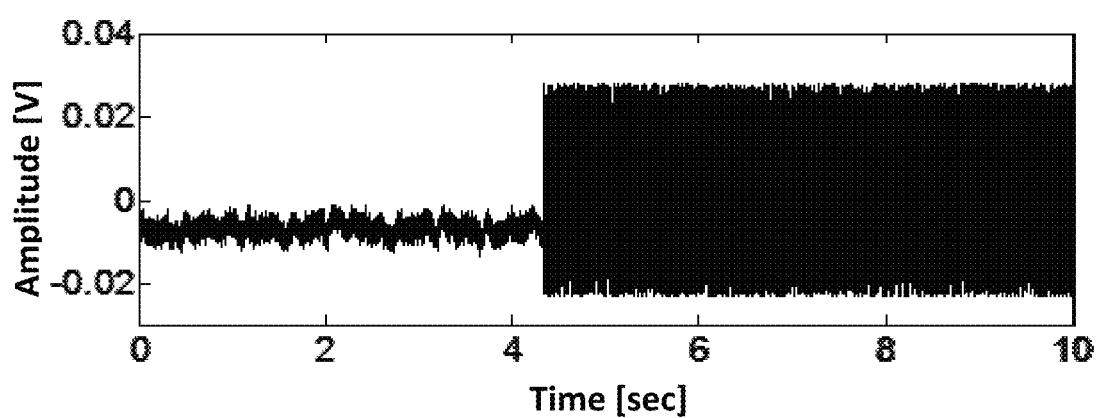
FIG. 13 shows application of a bitwise "shift-left" operation to the signal in FIG. 12. The amplitude of the GMF-interference decreased approximately 50-fold.

In one embodiment of the present invention, voltage division is applied to the "raw", unfiltered signals as the first, pre-processing step, in order to prevent amplifiers' saturation (FIG. 11). This pre-processing step is required for data collection during MR-scan using Filterbank I (see above). The system of present invention includes a set of two pre-processing filterbanks or filtering procedures (Filterbank P1 and Filterbank P0) that can be switched using an electronic, mechanical or software-controlled (programmable) switch. Filterbank P1 includes voltage-dividing resistors, whereas Filterbank P0 includes only "zero-Ohm" resistors or simple wires. When Filterbank P1 is switched on, the signals undergo voltage division, which is usually associated with increased amount of signal's noise, which can be filtered, using analog or programmable filters.

This signal conditioning using bitwise operations includes the following operations:
- A. To filter out GMF-signal, the most significant bits are discarded, because the high-amplitude GMF-signal is predominantly contained in the most significant bits. This is achieved using a bitwise "shift-left" operation (which is analogous to voltage multiplication) and discarding the "upper-most" (most significant) bits. In one embodiment of the present invention, this operation is implemented using a DSP. In another embodiment it is implemented using an amplifier (or a charge-pump) to multiply the signal, a comparator for checking the resulting voltage, an operational amplifier for subtracting the part of the signal that exceeds a certain threshold, and an analog-to-digital (A/D) converter. In a third embodiment, it is implemented using and A/D converter with serial control (e.g., Texas Instruments TLC2543C, TLC25431, or TLC2543M), in which the upper-most bits are discarded.
- B. Similarly, to extract a "clean" GMF-signal, the least-significant (right-most) bits are discarded. This is achieved using a bitwise "shift-right" operation (analogous to voltage division). In different embodiments of the present invention, this operation is implemented using a DSP, an A/D converter with serial control (e.g., Texas Instruments TLC2543C, TLC25431, or TLC2543M), in which the least-significant bits are discarded) or analog circuitry (utilizing resistors or charge pumps for voltage division), as described above. Subtracting the resulting "clean" GMF-signal from the original ("raw") signals produces a "clean" physiological (ECG) signal and vice versa.
- C. Filtering procedures (low-pass, high-pass, notch or band-pass) are applied to the output signal obtained after the bit-shift operation above.

Figure 14:
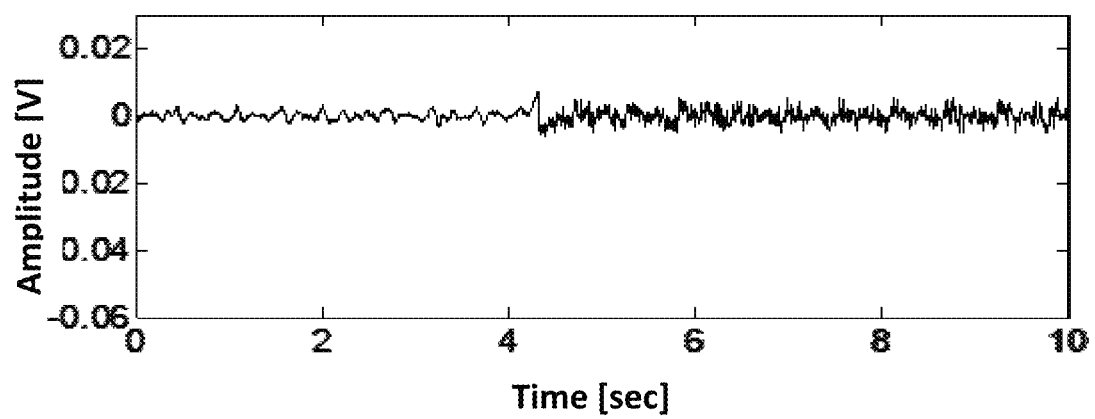
FIG. 14 shows application of subsequent band-pass filtering (the $4^{th}$ order, band-pass Butterworth filter with a 1-60 Hz pass-band) applied after the bitwise "shift-left" operation in FIG. 13.
Figure 15:
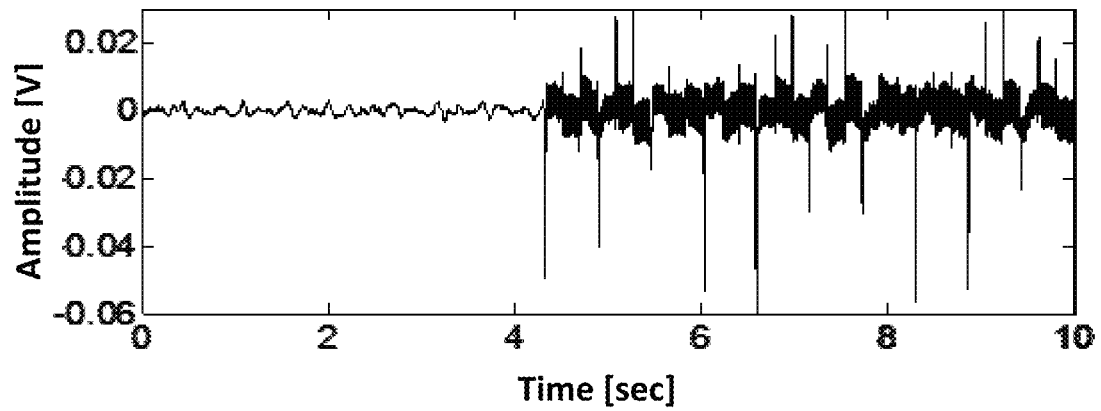
FIG. 15 shows application of the same band-pass filtering as in FIG. 14, which was applied to the original signal (i.e., bypassing bitwise shift operation shown in FIG. 13). Note that the low-amplitude signals are identical during the first 4 sec of the recordings (before the MR-scan). However, during the MR-scan, the two-step conditioning procedure described above (FIGS. 13 and 14) provides substantially cleaner signal (i.e., smaller interference), as compared with a simple band-pass filtering shown in FIG. 15.

FIG. 12-15 show application of this procedure for filtering of GMF-interference from electrophysiological recordings obtained during real-time Steady-state, Free-precession (SSFP) pulse sequence with short "Time-to-repeat" (TR=2.44-2.7 ms) and "Time-to-echo" (TE=1.22-1.35 ms), which are commonly used in the interventional cardiovascular MM. The raw (unamplified and unfiltered) signal shown in FIG. 12 was recorded using surface ECG electrodes, which were attached to a precordial chest region (corresponding to the ECG lead II position). The MR-scanning was initiated, approximately, 4 sec after the beginning of the recording and was associated with a large-amplitude GMF-interference. A bitwise "shift-left" operation decreased the amplitude of the GMF-interference approximately 50-fold (FIG. 13), but did not affect the low-amplitude patterns, which were represented in the least-significant ("rightmost") bits. FIG. 14 shows application of subsequent band-pass filtering (the $4^{th}$ order, band-pass Butterworth filter with a 1-60 Hz pass-band) applied after the bitwise "shift-left" operation, whereas FIG. 15 shows application of the same band-pass filtering procedure applied to the original signal (i.e., without prior bitwise shift operation). Note that the low-amplitude signals are identical during the first 4 sec of the recordings (before the MR-scan). However, during the MR-scan, the two-step conditioning procedure described above (FIG. 14) provides substantially cleaner signal (i.e., smaller interference), as compared with a simple band-pass filtering (FIG. 15).

IV. Filtering GMF and Magneto-Hydrodynamic Effects Using Signal Reconstruction

Filtering GMF-interference and reconstructing ECG waveforms (or other physiological signals) includes the following steps (and their variations):
- A. To obtain "clean", diagnostic ECG signals, a diagnostic ECG is recorded using Filterbank I outside the MR-magnet bore.
- B. Keeping subject's position and the distance from the MR-magnet unchanged, a second (non-diagnostic) ECG is recorded using Filterbank II.

C. For each ECG lead, patient-specific transfer coefficients b are computed between the diagnostic ECG signal (waveform), y, recorded in section A. (#1) and the corresponding non-diagnostic ECG signal, X, recorded in section B. (#2), as a solution to a linear regression problem. Specifically, for each ECG-lead, y=Xb+e, where b are the regression weights or coefficients that need to be determined and e are measurement errors. Omitting the measurement errors e in order to find an approximate form of the solution:

$$b=(X^TX)^{-1}X^Ty,$$

where $X^T$ denotes X transposed. The two signals (waveforms), X and y, are synchronized using the fiducial points (e.g., the ECG R-peak) or maximum cross-correlation between the two signals. This method works reasonably accurately when the measurement errors e are small and can be neglected.

However, in a real-life setting, the measurement errors e are relatively large, and the measured signal often contains significant amount of noise. To minimize the magnitude of noise, the present invention utilizes truncated singular value decomposition (SVD), of a square matrix $\tilde{X}^T\tilde{X}$, which is constructed from the measured signal, $\tilde{X}$, as a time-aligned series of physiological events (e.g., using the R-peaks of consecutive cardiac complexes in the ECG signal), and $\tilde{X}^T$ denotes $\tilde{X}$ transposed. The SVD is equivalent to the Principal Component Analysis and Karhunen-Loeve decomposition, which represent linear orthogonal decompositions, in which the basis vectors (eigenvectors or eigenfunctions) with the smallest weights (eigenvalues) are truncated. The truncation is based on the idea that the eigenvectors associated with the largest eigenvalues correspond to the measured signal, whereas those associated with small eigenvalues correspond to measurement noise. (Shusterman U.S. Pat. Nos. 8,388,530; 7,801,591 and 7,485,095; Odille et al. *Noise Cancellation Signal Processing Method and Computer System for Improved Real-Time Electrocardiogram Artifact Correction During MRI Data Acquisition. IEEE Transactions on Biomedical Engineering*, Vol 54, No. 4 pp 630-40 (April 2007).

$$X^+=(\tilde{X}^T\tilde{X})^{-1}\tilde{X}^T=(U\Sigma V^T)^{-1}\tilde{X}^T=(V\Sigma^{-1}U^T)\tilde{X}^T\sim(V\tilde{\Sigma}^{-1}U^T)\tilde{X}^T$$

where $X^T$ is the transpose of X and $\tilde{\Sigma}$ is the truncated SVD of the diagonal matrix $\Sigma$ of singular values (eigenvalues), in which the singular values that are less than a certain threshold are set to zero, reducing the rank of the associated matrix $(V\tilde{\Sigma}^{-1}U^T)$, which yields the following estimate of the regression coefficients:

$$b\sim(V\tilde{\Sigma}^{-1}U^T)\tilde{X}^Ty$$

The properties of this linear orthogonal transform are well established. In particular, it is known that the transform provides a least-squares solution using the smallest number of the basis vectors associated with the largest eigenvalues. (Shusterman U.S. Pat. Nos. 8,388,530; 7,801,591 and 7,485,095). This procedure is similar to signal averaging, which is also used to reduce the impact of noise in the method of present invention.

D. The patient is moved inside the MR-magnet bore, and the signals (e.g., ECG, EEG, EMG, blood pressure, pulse oximetry) are recorded using Filterbank I. The signals are affected by the magneto-hydrodynamic effect [MHE] due to the circulation of magnetized blood in subject's body. These signals are referred to as the MHE-ECG, MHE-EEG, MHE-EMG, MHE-pressure, etc.

E. Keeping the patient position unchanged inside the MR-magnet bore, the signals are recorded using Filterbank II.

F. A patient-specific transfer matrix is constructed between the signals recorded in #4 and #5 above. The two signals (waveforms) are synchronized using the fiducial points (e.g., the ECG R-peak) or maximum cross-correlation between the two signals, as described above. For each ECG lead, patient-specific transfer coefficients are calculated between the diagnostic ECG signal recorded in section A. (#1) and the corresponding non-diagnostic ECG signal recorded in section B. (#2), using linear regression and truncated SVD, as described above (see section C. [#3]).

G. During the MR-scan, Filterbank II is used to filter out interference generated by the MR-gradients in real time. Then the diagnostic MHE-ECG is reconstructed using the patient-specific transfer matrix as described in section F. (#6) above. To evaluate reconstruction accuracy, the reconstructed MHE-signals are compared with those recorded using Filterbank I in the absence of MR-gradients (when the scanning is not performed), as described in section D. (#4) above, using cross-correlation and/or other statistical metrics.

If the reconstruction accuracy is not sufficiently high, the process of computing the transfer matrix $X^+$ is treated as a minimization problem, with the goal (objective function) of minimizing the difference (and/or maximizing cross-correlation) between the two signals, using at least one method selected from optimization algorithms. The optimization methods include simplex algorithm, iterative methods (e.g., Newton's method and quasi-Newton method, finite-difference method and other methods of approximation theory and numerical analysis, methods that evaluate gradients using finite differences, sequential quadratic programming, approximate Hessians, gradient descent or steepest descent methods, ellipsoid method, simultaneous perturbation stochastic approximation, interpolation methods and global convergence methods) and heuristic algorithms (e.g., memetic algorithm, differential evolution, differential search, dynamic relaxation, genetic algorithms, Hill climbing, Nelder-Mead algorithm, reactive search optimization).

H. To reconstruct a "clean" (free of MHE) diagnostic ECG, the reconstructed signals described in section G. (#7) above are multiplied by the corresponding transfer matrix described in section C. (#3) above. The reconstruction accuracy is evaluated by comparing reconstructed diagnostic, "clean" signals with those measured directly (see #1 above), using the cross-correlation and/or other statistical metrics. If the reconstruction accuracy is not sufficiently high, the process of computing the transfer matrix $X^+$ is treated as a minimization problem, with the goal (objective function) of minimizing the difference (and/or maximizing the cross-correlation) between the two signals, using at least one method described in section G. (#7) above.

Figure 16:
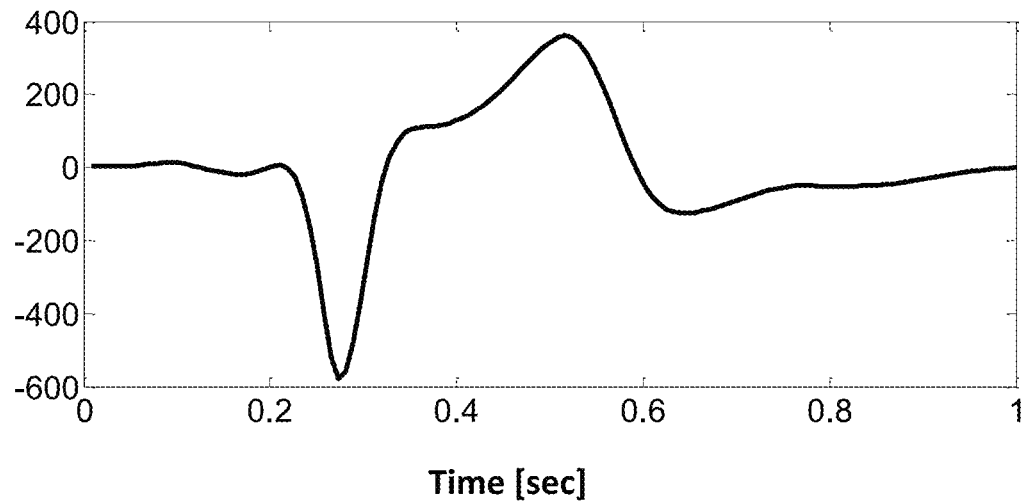
FIG. 16 is an example of clean, diagnostic ECG signal (Lead II) recorded outside the magnet bore.
Figure 17:
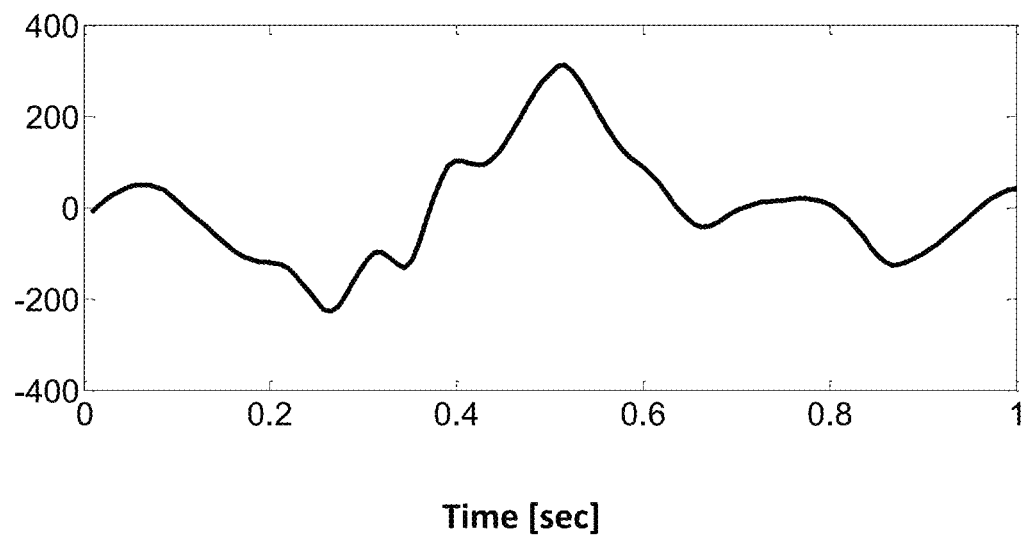
FIG. 17 is the signal in the same ECG lead after the subject was moved inside the magnet bore; changes in the signal are caused by the Magneto-hydrodynamic effect (MHE).
Figure 18:
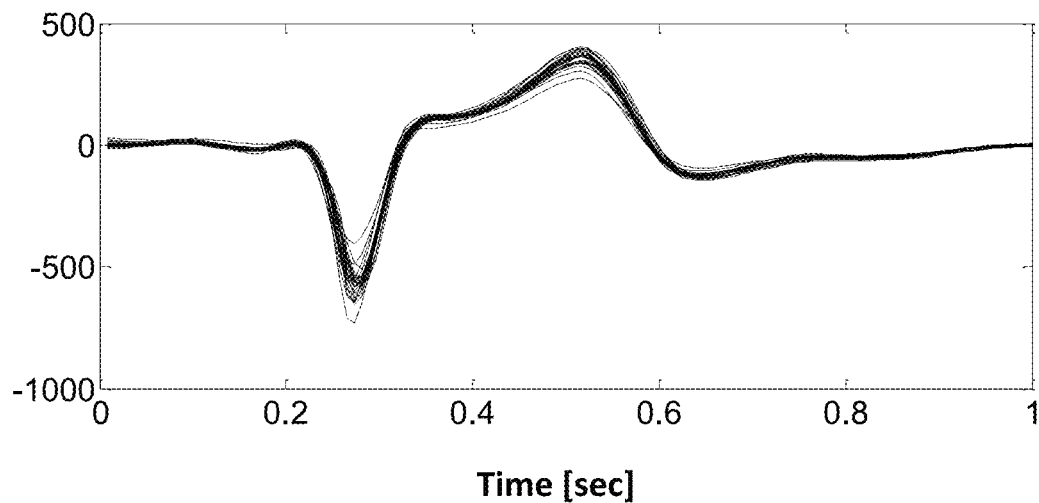
FIG. 18 shows the cardiac complexes that were reconstructed, using the MHE-ECG and the processing steps described in section "4. FILTERING GMF AND MAGNETO-HYDRODYNAMIC EFFECTS USING SIGNAL RECONSTRUCTION".
Figure 19:
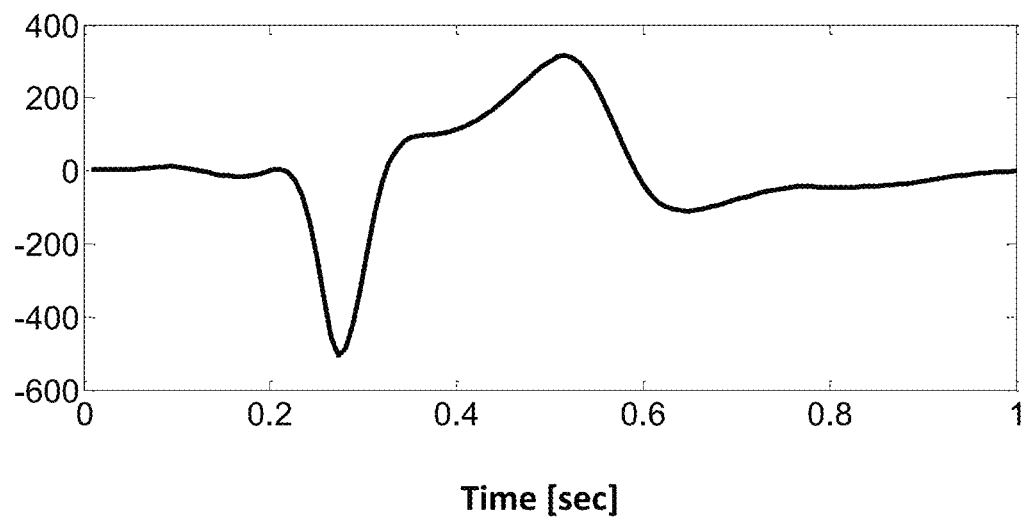
FIG. 19 is an average reconstructed ECG complex.
Figure 20:
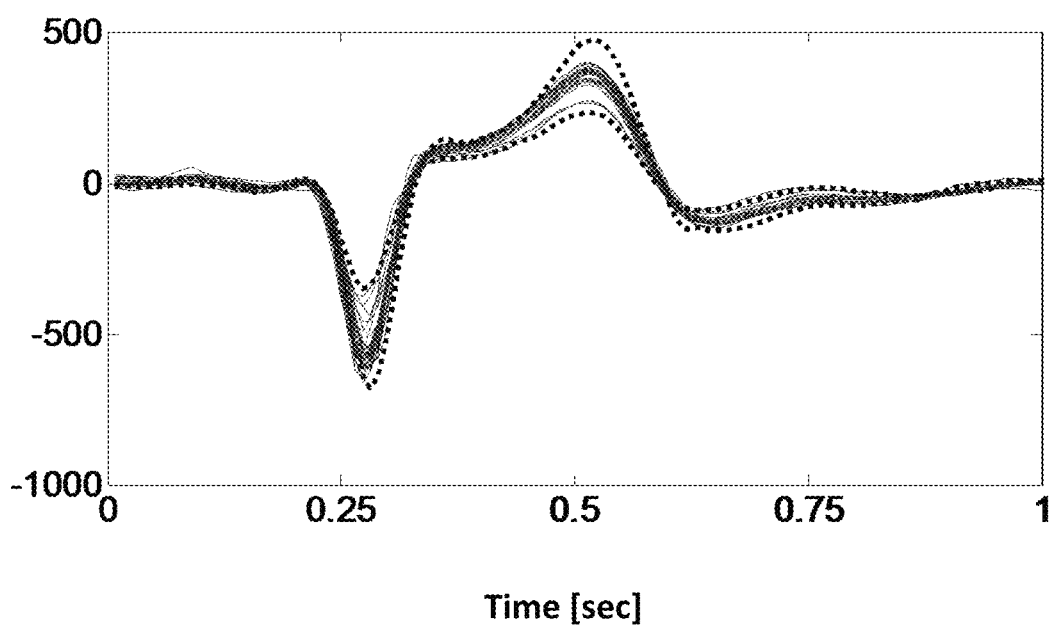
FIG. 20 shows reconstructed ECG complexes (solid lines) superimposed on the range of variations in measured ECG complexes (dashed lines).

FIG. 16-20—illustrate the processing steps described above. FIG. 16 shows an example of clean, diagnostic ECG signal (Lead II) recorded outside the magnet bore. FIG. 17 shows the ECG signal in the same lead after the subject was moved inside the magnet bore; changes in the signal are caused by the MHE. FIG. 18 shows the cardiac complexes that were reconstructed, using the MHE-ECG and the processing steps described above. FIG. 19 shows an average reconstructed ECG complex. To compare measured and reconstructed ECG complexes, FIG. 20 shows reconstructed ECG complexes (solid lines) superimposed on the range of variations in measured ECG complexes (dashed lines).

The magnitude of MHE may change due to changes in blood pressure, arterial pressure wave, blood volume or blood flow. To track changes in these parameters, the system of present invention uses at least one measurement selected from the MR-based measurements of blood flow, arterial pressure waves and/or blood volume, intra-arterial blood pressure, intra-cardiac blood pressure, venous blood pressure, noninvasively measured blood pressure, arterial and/or intra-cardiac pressure waves measured by photoplethysmography, plethysmography, electrical impedance, pulse oximetry, accelerometry, acoustic waves, ultrasound, infrared and other optical, mechanical and electrical signals obtained from subject's body.

If significant changes in these signals are detected, the transfer matrix $X^+$ is further adjusted, using at least one of the following methods:
  A. The patient is moved out of the MR-magnet bore, and a clean (free of MHE), diagnostic ECG is recorded; a new transfer matrix $X^+$ is obtained as described above (see #3).
  B. The patient remains inside the magnet bore of the MR-scanner, while the transfer matrix $X^+$ is adjusted using statistical relationships between the changes in blood pressure/flow and MHE. The statistical relationships are obtained from an individual subject's data and/or a group (population) of subjects.

The reconstruction process described above may lead to inaccurate results if the shape of the ECG waveforms deviates from the dominant waveforms, which have been used for computing the transfer matrix $X^+$. Because the dominant ECG waveform in most subjects originates from the sinus node (i.e., sinus beats), the transfer matrix $X^+$ is based on the sinus beats in most subjects. This transfer matrix may not be accurate for reconstructing ectopic beats (e.g., premature atrial complexes, PACs, and premature ventricular complexes, PVCs). The system of present invention allows users to display and compare both unreconstructed and reconstructed signals, as they are received. It also allows viewing and comparing newly received data with templates (waveforms, patterns) obtained from multiple, averaged or median cardiac beats/complexes (e.g., sinus beats, PVC, PAC).

Optimized Wireless Data Transmission

This invention provides a novel and efficient way to obviate the limits of data-transmission-rate (speed) of wireless communication, as well as its inherent vulnerability to transmission losses, delays and complete interruptions, which create significant technical difficulties for the development of multichannel, wireless monitoring systems. It provides fast and reliable data transmission for multiple data channels in real time, using the following improvements:
  I. Parallel Transmission of Multiple Channels and/or Groups of Channels Using Several Wireless Transmitters
    The key elements of this invention include:
      a. utilizing a modular system architecture with the same or similar data-acquisition and processing modules and a wireless transmitter/receiver on each module (or associated with each module),
      b. distributing wireless communication between the wireless transmitter/receiver associated with different modules (instead of a single transmitter/receiver, which is traditionally used in wireless systems as a wireless alternative to a cable transmission), and
      c. synchronizing the modules by passing synchronization signals (i.e., time markers) to one (or more) data channels of all (or some) modules.

Data Synchronization

Data received by different modules can be synchronized by time markers (stamps), which include short-time, discrete pulses or continuous waveforms (e.g., sinusoidal waves with a constant frequency). The time markers can be generated by one module and transmitted to other modules; they can be also generated by a data-synchronization module or a motherboard and transmitted to all modules. The time markers are recorded by each Module into a separate data-synchronization channel and transmitted wirelessly along with other data-channels to the data-receiving station. The software on the receiving station (e.g., computer/laptop/smart phone) utilizes the time markers to synchronize the data received from different modules. They synchronization is achieved by time-aligning the time markers, as well as simultaneously acquired data channels received from all modules.

II. Wireless Transmission Using Multiple Transmitters that Operate in Different Frequencies (Frequency Ranges) to Prevent Transmission Loss/Failure A medical device of this invention improves reliability of wireless transmission (which may become unreliable in the presence of electromagnetic interference, electromagnetic shields or changing distance and position of the transmitter relative to a receiver). Distribution of wireless transmission into several independent data streams can provide backup for potential failures in some of the wireless transmission links.

Figure 1:
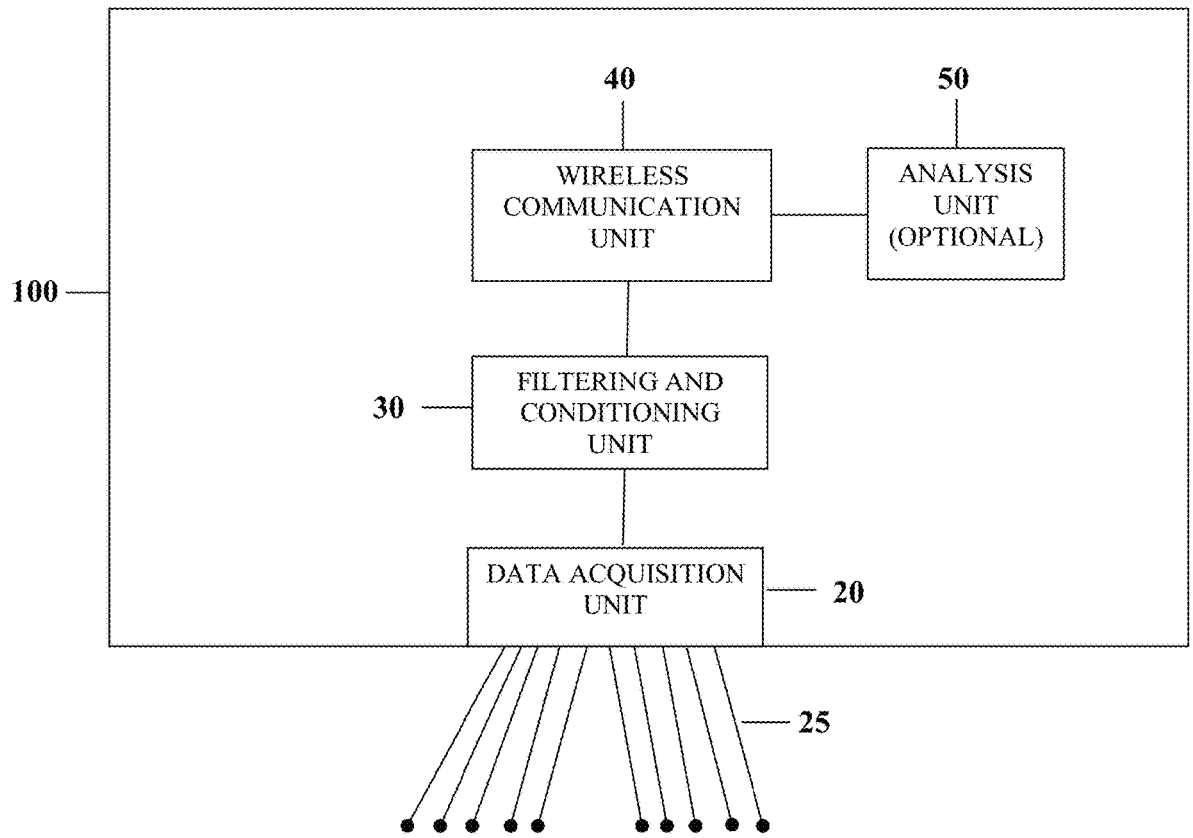
FIG. 1 is a block-diagram of an embodiment of the system architecture that includes a data-acquisition module (unit), a wireless communication (transmission) module, a filtering and conditioning module, and an optional analysis module. Note that all these modules are integrated into a single compact, mobile unit.

FIG. 1 is a block-diagram of a preferred embodiment of a medical device 100 of this invention. The device consists of a data-acquisition 20 unit (herein, the terms unit, module, circuitry, part, section are used interchangeably and may refer to electronic hardware, firmware and software) that may have several cables with electrodes 25 for attachment to a subject (not shown) to receive ECG or other physiological signals in real-time, a filtering and conditioning module 30, a wireless communication unit 40 (with optional data synchronization unit/circuitry/firmware) and an optional analysis unit 50. The acquisition unit receives physiological signals through the electrodes 25 that are connected to a subject. As used herein, subject means a human or an animal.

Block-diagrams of several configurations of the data-acquisition and filtering parts of a medical device of this invention are shown in FIG. 6-10.

Figure 6:
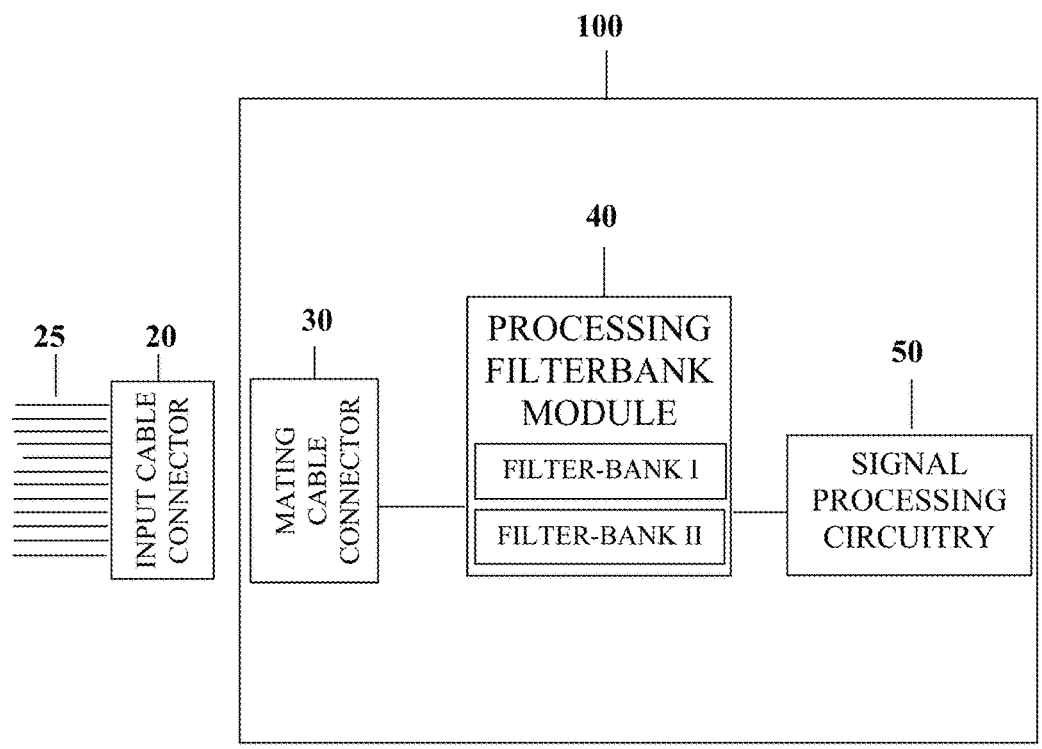
FIG. 6 is a block-diagram of the system configuration with two switchable filterbanks. The filterbanks are selected using a mechanical, electronic or programmable switch.

In FIG. 6, physiological signals are received through cables/electrodes 25, which are attached to a subject on one side and an input cable connector 20 on another side. The input cable connector attaches to a medical device of this invention through a mating cable connector 30, which transmits the acquired signals to a processing filterbank module 40. The filterbank module 40 consists of at least two switchable filterbanks (Filterbank I and II), which are selected using a mechanical, electronic or programmable switch. The signals filtered through the selected filterbank are passed to the signal processing circuitry 50 for further processing and analysis.

Figure 7:
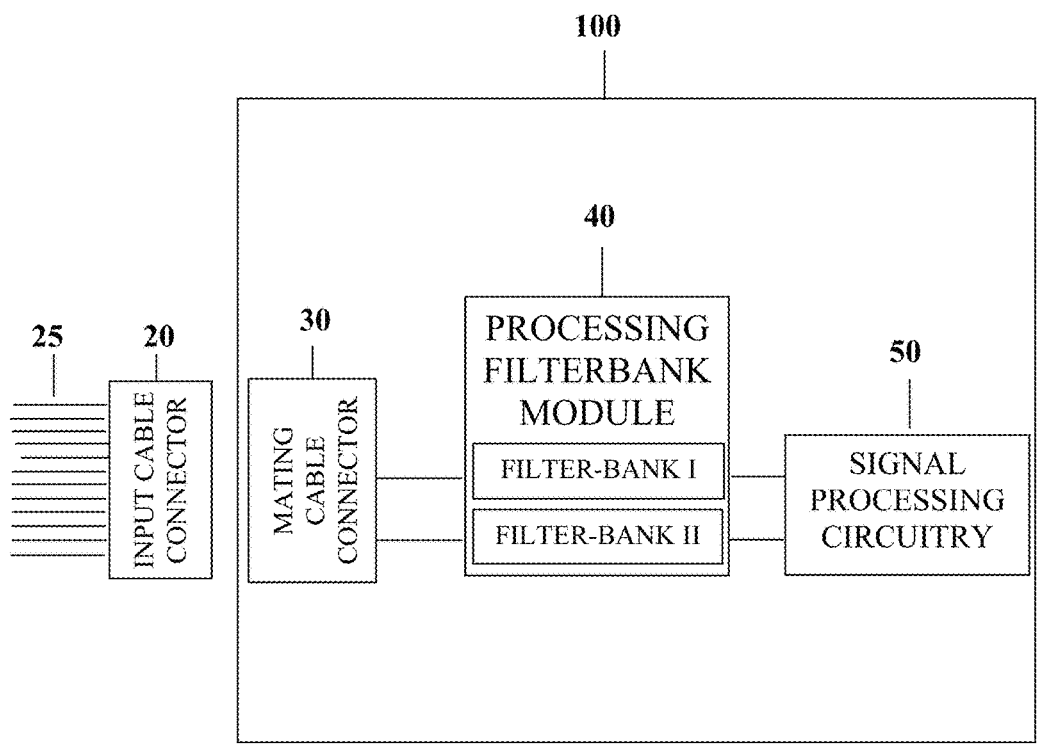
FIG. 7 is a block-diagram of the system configuration with two parallel filterbanks; all data channels are filtered through two different filterbanks. This configuration doubles the number of data channels, because the two filterbanks produce two parallel data streams that are passed to the Signal Processing Circuitry (50).

FIG. 7 is a block-diagram of the system configuration, which is similar to that in FIG. 6. However, in this configuration the filterbanks in module 40 are configured to provide parallel filtering, which doubles the number of data channels that are passed to the signal processing circuitry 50. The two parallel data streams are necessary for determining the transfer function between the two data streams and reconstruction of diagnostic quality signals in the presence of GMF-interference and MHE, as described in the Summary of the Invention (section 2. Filtering GMF using parallel filterbanks.)

Figure 8:
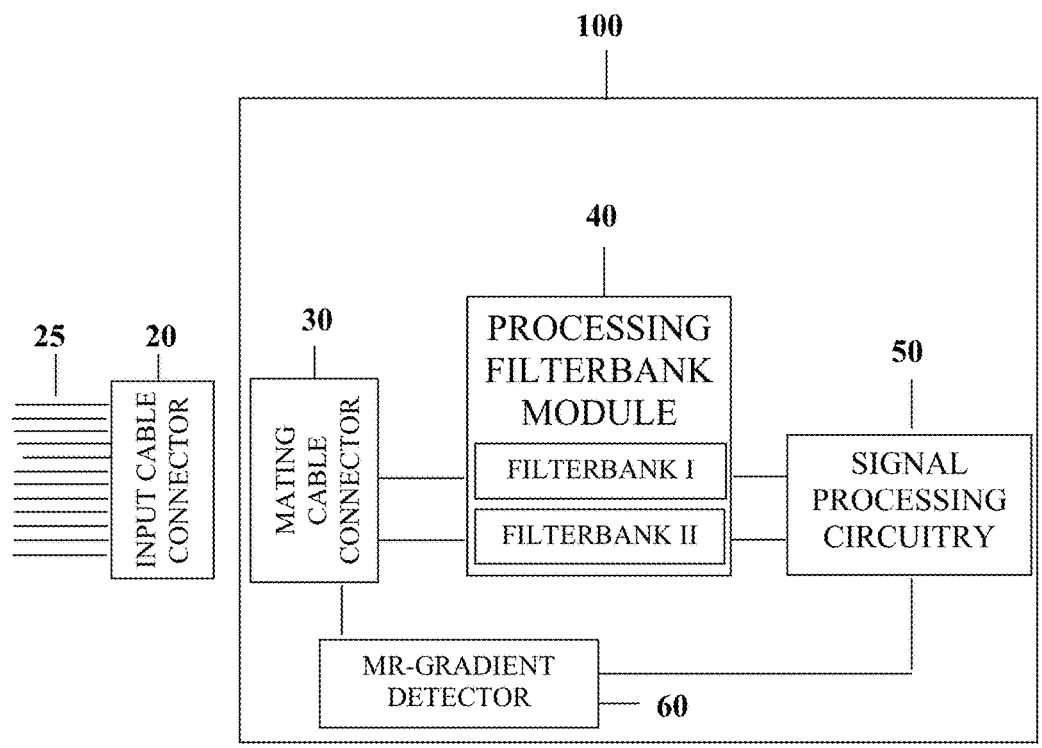
FIG. 8 is a block-diagram of the system configuration with an MR-gradient detector (60), which receives the signals from the Mating Cable Connector (30) and passes the GMF-detection information to the Signal Processing Circuitry (50).

FIG. 8 shows a block-diagram of system configuration, which is similar to that in FIG. 7 but also includes the MR-gradient detector 60, which receives the signals from the Mating Cable Connector 30 and passes the GMF-detection information (about the beginning and end of GMF-events) to signal processing circuitry 50.

Figure 9:
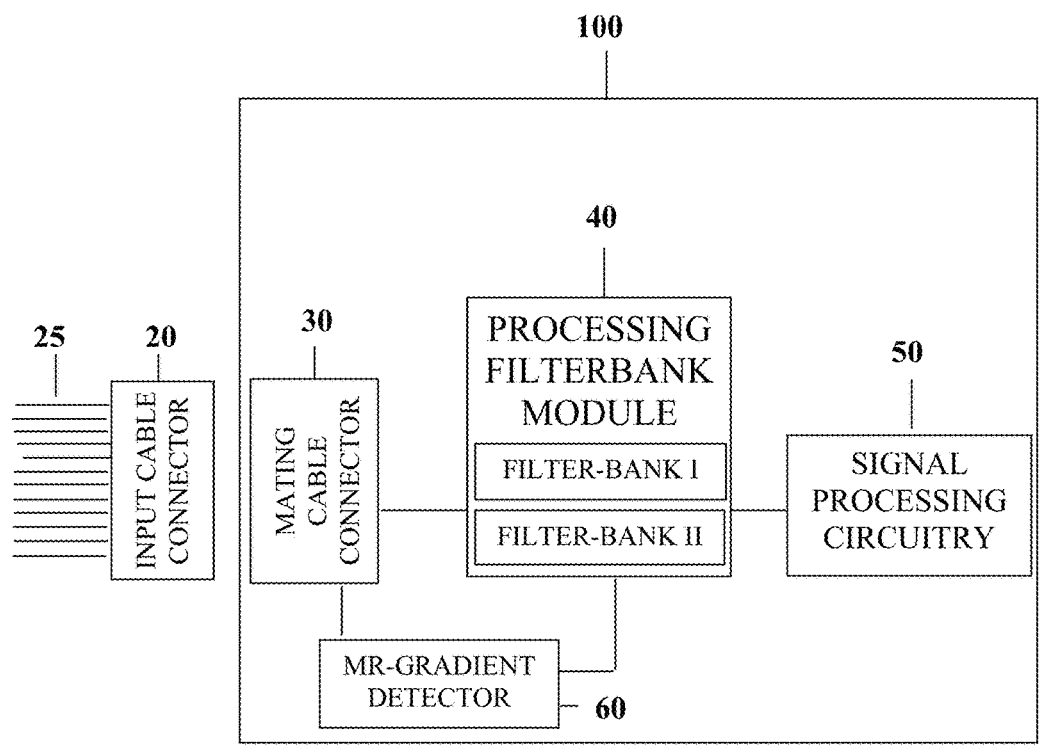
FIG. 9 is a block-diagram of the system configuration with an MR-gradient detector (60), which receives the signals from the Mating Cable Connector (30) and passes the GMF-detection information to the Processing Filterbank Module (40).

FIG. 9 is a block-diagram of the system configuration, in which an GMF detector 60 passes the GMF-detection information to the processing filterbank module 40. This configuration allows programmable switching of the filterbanks in module 40 at the time points of GMF-detection based on the information received from the GMF-detector 60. The programmable switching is, preferably, implemented using digital signal processing, which provides very short switching time.

Figure 10:
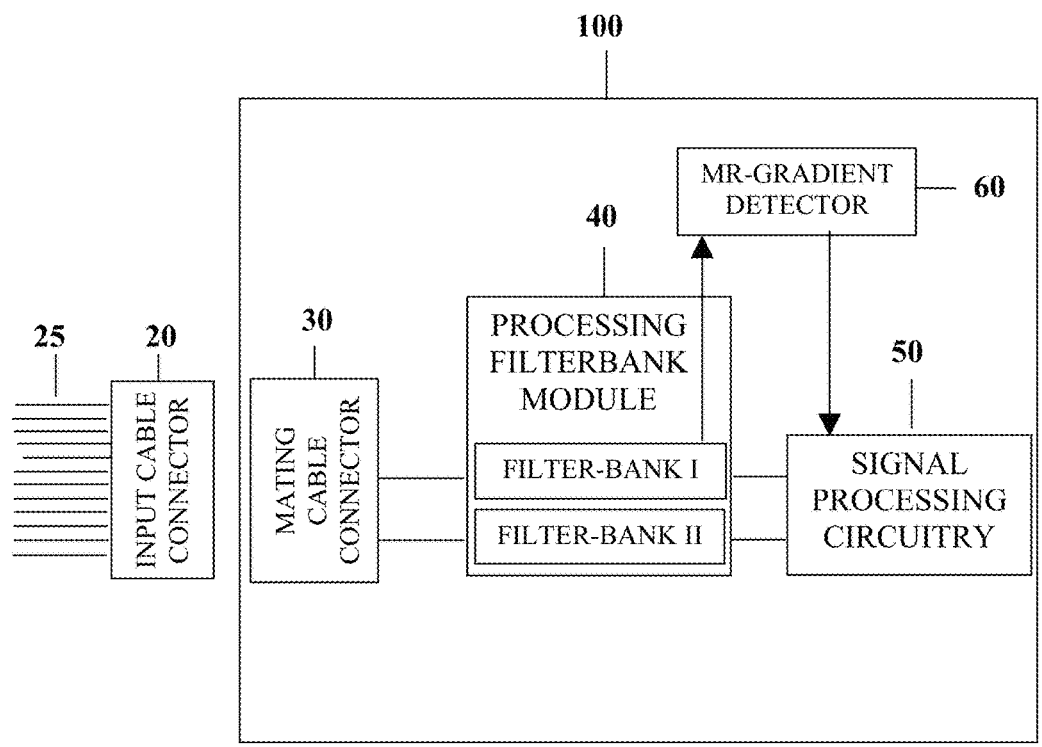
FIG. 10 is a block-diagram of the system configuration with an MR-gradient detector (60), which receives the signals from the Filterbank I and passes the GMF-detection information to the Signal Processing Circuitry (50).

When the level of GMF is very high a medical device of this invention uses an MR-gradient detector 60, which is connected to filterbank module 40, as shown in FIG. 10, to prevent amplifiers' saturation. To further enhance filtering of powerful GMF-levels, a preprocessing filterbank module 70 is incorporated as shown in FIG. 11. Module 70 includes at least two filterbanks; filterbank P1 provides reduction of signal's magnitude, whereas filterbank P0 passes signals through without any changes. The procedures for reducing signal magnitude in filterbank P1 include voltage division and bitwise operations, as described in the Summary of the Invention (section 3. Filtering GMF using bitwise operations, signal multiplication and division).

Figure 21:
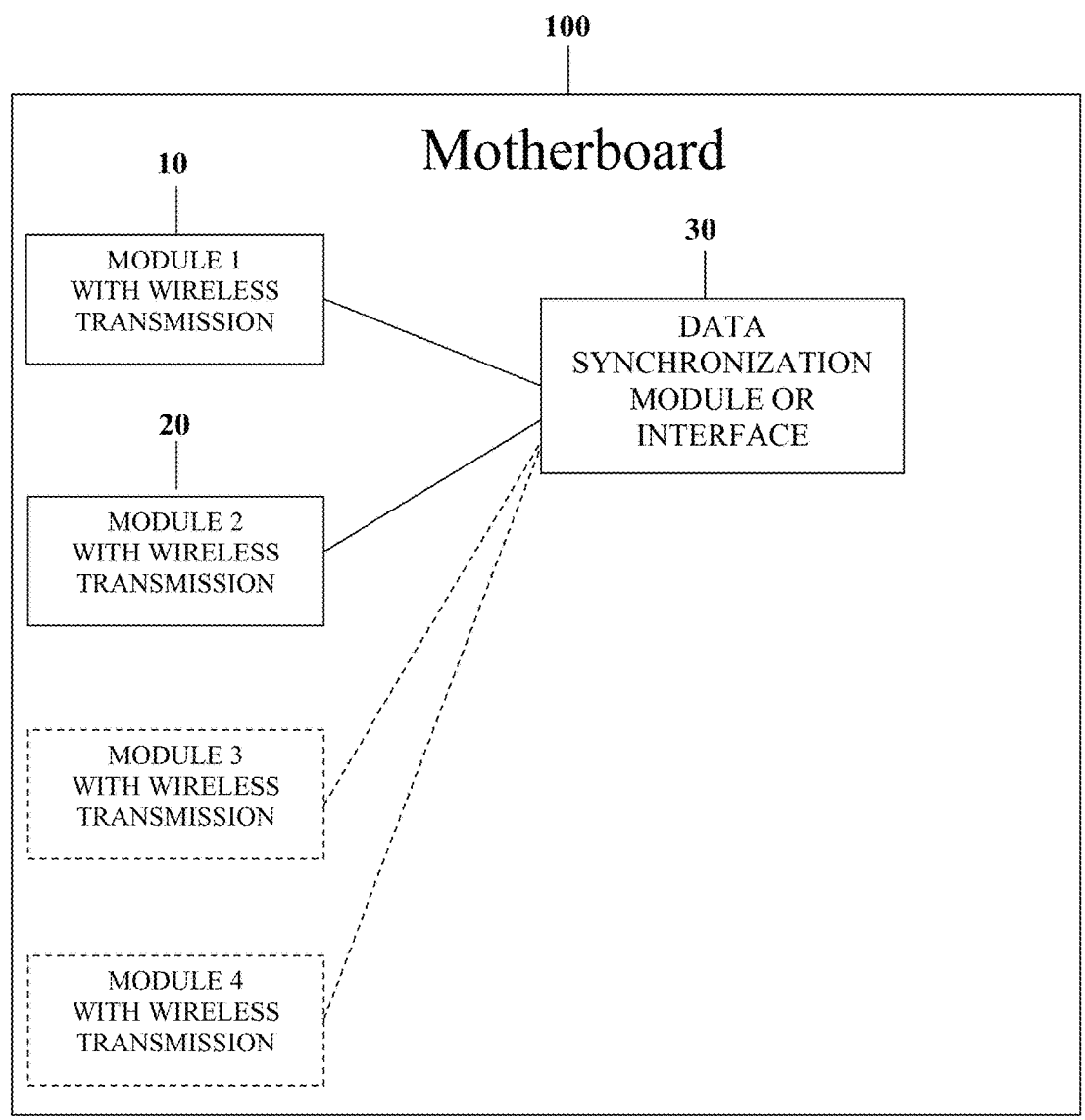
FIG. 21 is a block-diagram of a system's embodiment with two data-acquisition and/or processing modules, as well as data-synchronization unit/interface.
Figure 22:
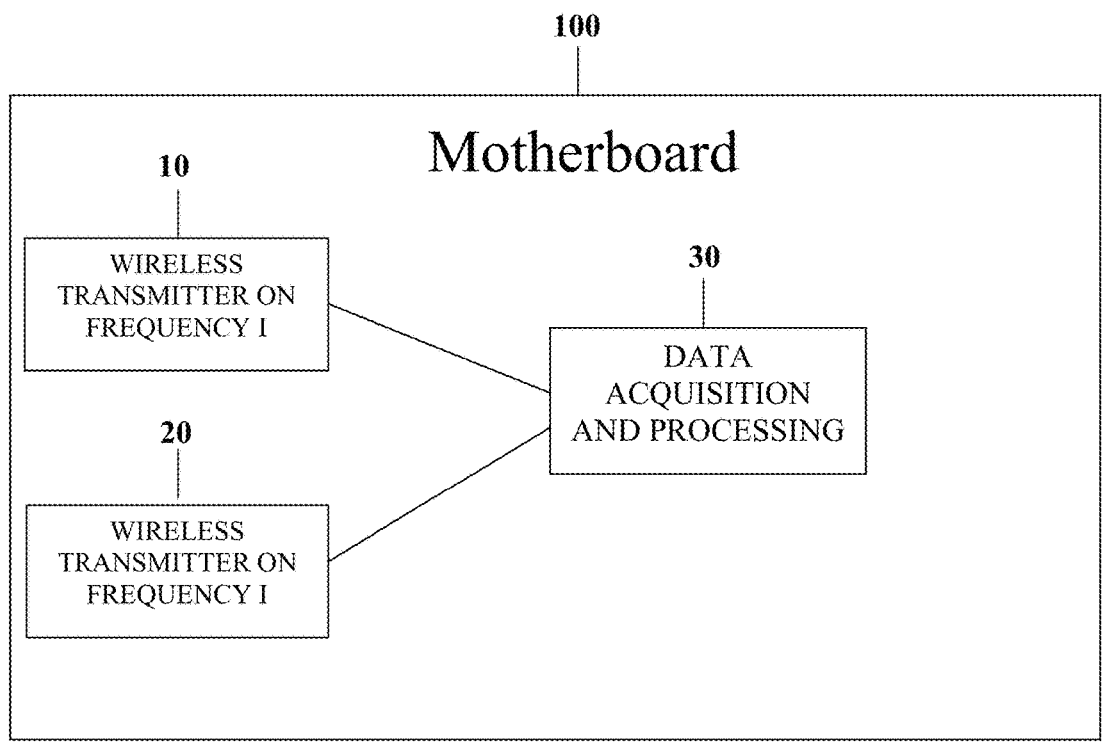
FIG. 22 is a block-diagram of a system's embodiment with two radio transmitters, which transmit data concurrently using two different frequency ranges to prevent data loss in case that one of the transmission frequencies fails.

Configuration of a wireless communication unit of a medical device of this invention, as well as data-synchronization unit/interface, are shown in FIGS. 21 and 22. In FIG. 21, each data acquisition module (module 10, module 20, etc.) has an associated wireless transmitter. Each module provides data acquisition and/or processing for some of the data channels, and has a wireless transmitter associated with it (e.g., Bluetooth, WiFi or Zigbee). For example, Module #1 provides multi-channel acquisition of ECG data, whereas Module #2 provides multi-channel acquisition of blood pressure and pulse-oximetry data. For systems with a big number of data channels (e.g., Cardiac Electrophysiology, EMG or EEG monitoring systems), the number of modules can be further increased, as required.

The wireless modules serve two purposes:
 a. an interface for programming data-acquisition parameters for each module (sampling rate, resolution, number of channels, duration of data acquisition, and data transmission mode [real-time transmission or recording to each module's memory card]), and
 b. real-time data transmission to a receiving station.

In this configuration, each module acquires and transmits data via its associated wireless transmitter, producing parallel data streams, which are aggregated, synchronized, processed and displayed at the receiving station (not shown). The modules are synchronized using a periodic impulse and/or frequency signal (with known frequency characteristics, e.g., a 1 kHz sine wave), which serve as time markers. These time markers are generated by module 1 or a separate data-synchronization module/interface 30 and recorded to the reference-data channel of all modules, along with simultaneously acquired data channels. Because the time markers are generated and recorded by each module simultaneously with other data channels, the receiving station synchronizes the data by time aligning the corresponding time markers (as well as simultaneously acquired data channels) in all modules.

FIG. 22 is a block-diagram of a system's embodiment with two radio transmitters, which transmit data using two different frequency ranges to prevent data loss in case that one of the transmission frequencies fails. In a preferred embodiment of a medical device of this invention, the same data are transmitted independently and concurrently by two (or more) transmitters using two different transmission frequencies (e.g., 2.4 and 5.2 GHz); this parallel transmission ensures that the data will be received by at least one receiver utilizing one of the transmission frequencies, even if the second transmission link fails (FIG. 22).

In another configuration of a medical device of this invention, wireless transmission includes intelligent, "on-demand" re-routing of data from failed wireless links (transmitters) to working ones. Examples of such wireless transmitters include: (i) transmitters of the same type (e.g., two Bluetooth transmitters), (ii) transmitters of different types (e.g., Bluetooth and Wi-Fi), and (iii) transmitters of the same type but with different transmission frequencies (e,g, Wi-Fi operating on 2.4 and 5.2 GHz).

Wireless transmitters of the same type often share the same transmission frequency range. For example, Bluetooth transmitters use ~2.4 GHz frequency range with adaptive frequency hopping, which may create interference between several Bluetooth radios transmitting data at the same time. To obviate this problem, the Bluetooth transmission protocols in one configuration of a medical device of this invention are adapted to the presence of other Bluetooth transmitters by dividing the transmission spectrum, thus avoiding interference between them.

Figure 23:
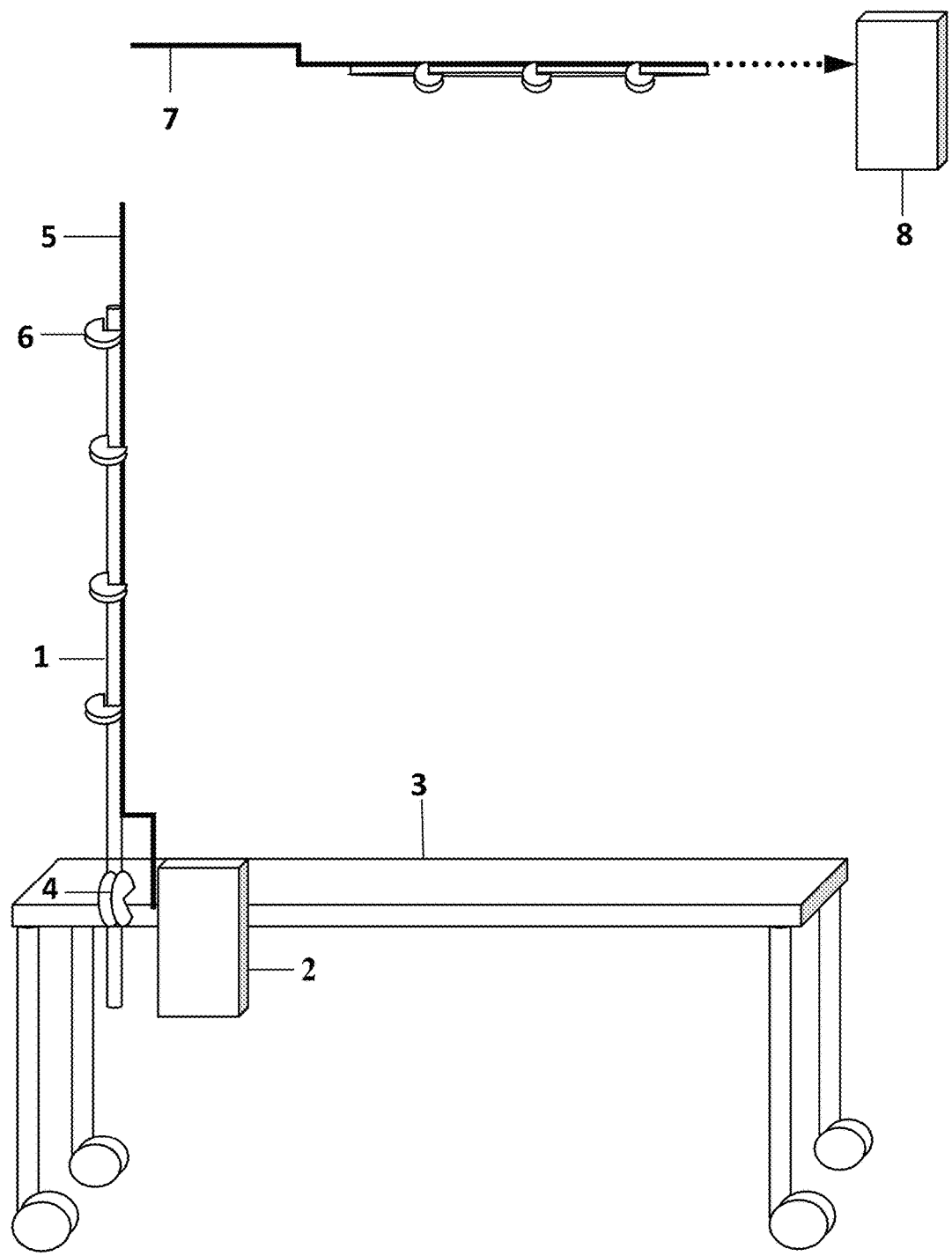
FIG. 23 shows a wireless antenna mount (1); a data-acquisition and wireless transmission unit of this invention (2) is attached to a mobile patient table (3) using a c-clamp (4). The wireless antenna (5) is attached to the antenna mount using a series of mounting hooks (6), c-clamps, or Velcro straps. Unit (2) transmits data wirelessly, using the transmitting antenna (5), to a receiving wireless antenna (7), which is mounted on the ceiling to provide substantially unimpeded wireless transmission for various locations of the patient table. The receiving antenna is connected to a wireless receiver unit (8), which can be located in the same room or in a different room. The wireless receiver unit can also include processing, analysis and display of the received physiological signals.

FIG. 23 shows one embodiment of this invention in which a wireless antenna mount (1) and a data-acquisition and wireless-communication (transmission) module (2) are attached to a mobile patient table (3) using a c-clamp (4) or some other mounting device. A wireless antenna (5) connected to module (2) is attached to the mounting pole (1) using a series of hooks (6), c-clamps, or Velcro straps. The mounting poles that can be used for mounting a wireless antenna include a lighting holder arm, a lighting stand and other types of stands.

Because the first antenna (5) stays with the patient table as the table (and the patient) is being moved during a procedure or between different procedure rooms, it provides uninterrupted wireless communication during patient (and patient-table) movement. The second antenna (7) is mounted on the ceiling or on the wall; it extends at least six feet above the floor to provide unimpeded communication with the first antenna (5) during table movement as well as during the movement of medical personnel and equipment around the table (bed). Thus, in this embodiment, wireless communication between the two antennas is carried out in the space (plane) at least six feet above the floor that is not affected by patient-table, personnel, or equipment movement. The second antenna (7) is connected to the receiving and processing unit/module (8), which is located in the same room (mounted on the ceiling or on the wall) or in another (e.g., adjacent) room.

Figure 24:
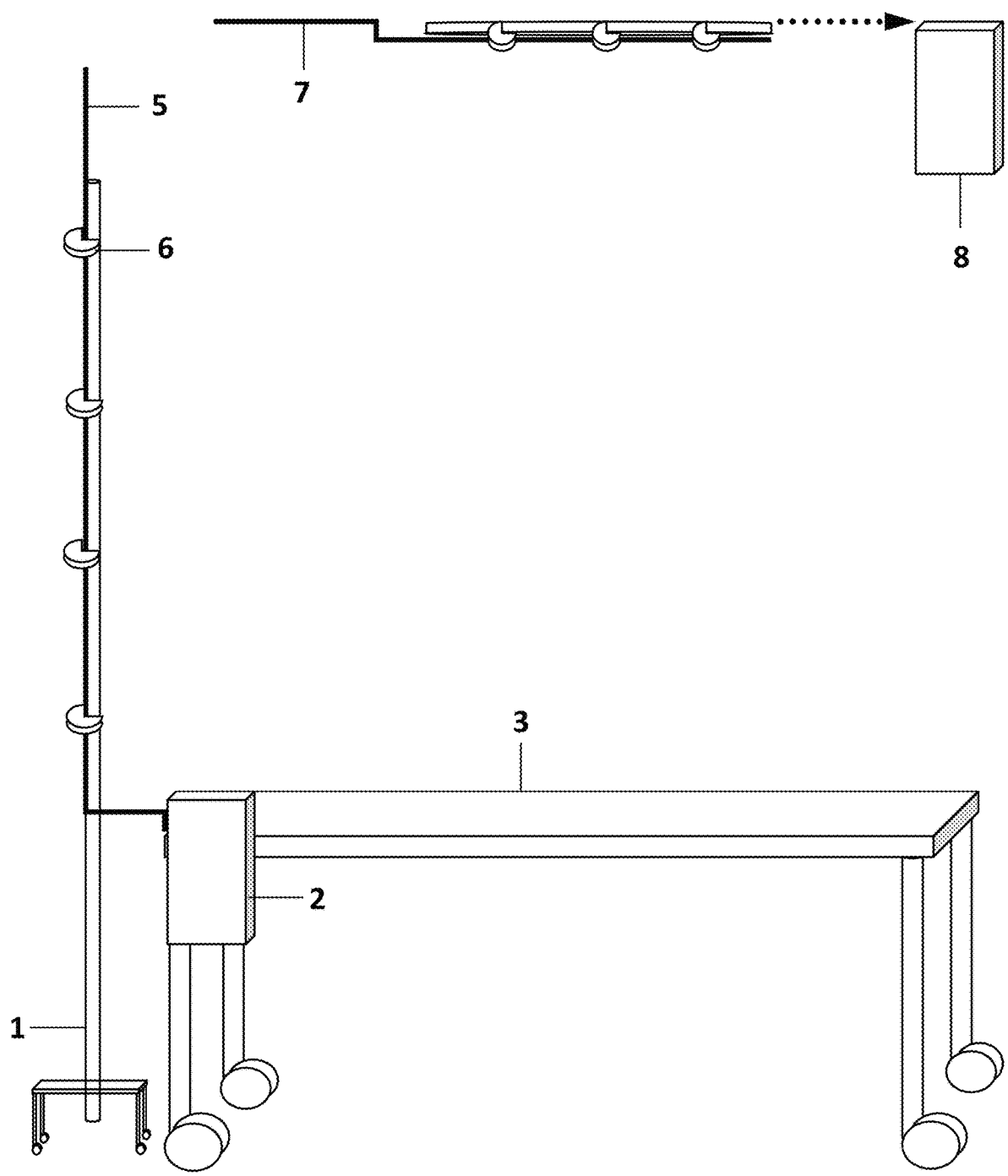
FIG. 24 shows a freestanding wireless antenna mount (1), which has its own stand on wheels. The data-acquisition and wireless-transmission unit (module) of this invention (2) is attached to a patient table (3) using a c-clamp or mounting device (not shown). The wireless antenna (5) is attached to the antenna mount using a series of mounting hooks (6), c-clamps, or Velcro straps. Unit (2) transmits data wirelessly, using the transmitting antenna (5), to a receiving wireless antenna (7), which is mounted on the ceiling to provide substantially unimpeded wireless transmission for various locations of the patient table. The receiving antenna is connected to a wireless receiver unit (8), which can be located in the same room or in a different room. The wireless receiver unit can also include processing, analysis and display of the received physiological signals.

FIG. 24 shows an embodiment of this invention in which a wireless antenna (5) is mounted on a freestanding mounting pole (1) and is secured using a series of hooks (6), whereas the data-acquisition and wireless-transmission unit (2) is attached to the patient table (3). The receiving antenna (7) is mounted to the ceiling or to the wall to provide uninterrupted communication with the transmitting antenna during various movement of the patient table and medical personnel. The receiving antenna is connected to the wireless receiver and processing unit (8).

Figure 25:
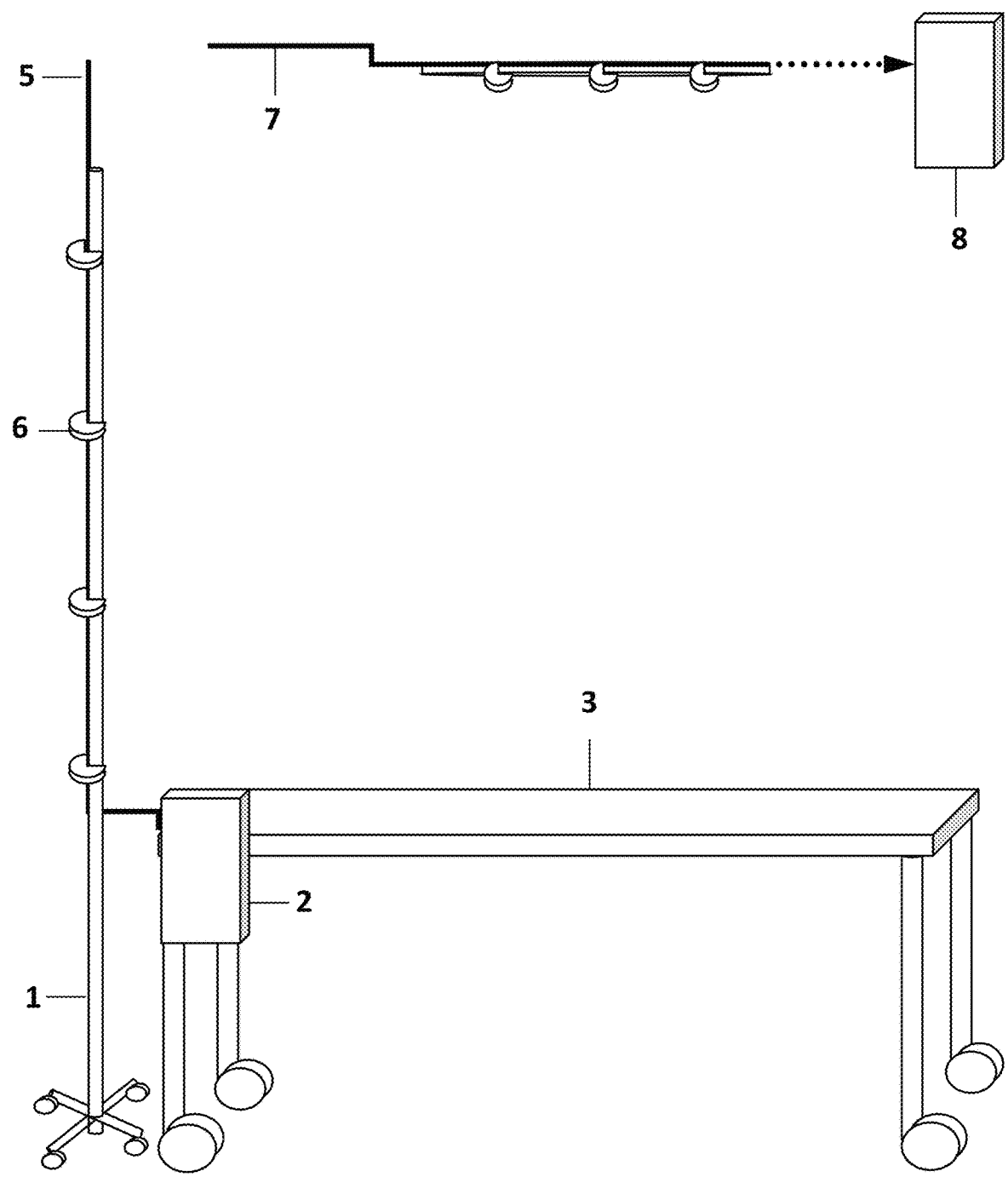
FIG. 25 shows a wireless antenna mount (1) mounted on an intravenous (IV) infusion pole (1), which can also be used for hanging IV fluid bags. The data-acquisition and wireless-transmission unit of this invention (2) is attached to a patient table (3) using a c-clamp or mounting device (not shown). The wireless antenna (5) is attached to the antenna mount using a series of mounting hooks (6), c-clamps, or Velcro straps. Unit (2) transmits data wirelessly, using the transmitting antenna (5), to a receiving wireless antenna (7), which is mounted on the ceiling to provide substantially unimpeded wireless transmission for various locations of the patient table. The receiving antenna is connected to a wireless receiver unit (8), which can be located in the same room or in a different room. The wireless receiver unit can also include processing, analysis and display of the received physiological signals.

FIG. 25 shows an embodiment of this invention in which a wireless antenna (5) is mounted on a freestanding intravenous (IV) infusion pole, which may also hold a hanging IV fluid bag (1), and is secured using a series of hooks (6), whereas the data-collection and -transmitting unit (2) is attached to the patient table (3). The receiving antenna (7) is mounted to the ceiling or to the wall to provide uninterrupted communication with the transmitting antenna during various movement of the patient table and medical personnel. The receiving antenna is connected to the wireless receiving and processing unit (8).

In one embodiment, the transmitting antenna extends to at least six feet above the floor to provide substantially unobstructed communication with at least one receiving antenna, which is also positioned at least six feet above the floor.

In one embodiment, the transmitting antenna is located below patient level to provide substantially unobstructed communication with at least one receiving antenna located on the floor surface (below the patient). In one embodiment, the frame of the patient table (bed) serves as a transmitting antenna.

In one embodiment, the transmitting antenna is fed through (mounted inside) a hollow pole, which can be also used for hanging IV fluid bags. In a preferred embodiment, the pole is mounted (connected) to the patient table. The antenna mount is attached to the patient table using, for example, a c-clamp, and stays with the patient table as the patient is moved during different procedures as well as between different procedure rooms.

An important aspect of this invention is adaptive filtering and signal conditioning implemented in a DSP module/unit. The DSP operations are adapted to the properties of EMI and recorded data (physiological signals), using:
  adaptive selection (control) of the channel (signal) for EMI detection;
  adaptive selection (control) of the detection parameters (e.g., magnitude and duration of the EMI peaks and the time interval between them), as described below;
  adaptive selection (control) of the channel (signal) for the detection of cardiac-activity waveforms (e.g., ECG QRS complexes); and
  adaptive selection (control) of the detection parameters for cardiac-activity waveforms (e.g., magnitude and duration of the ECG QRS complexes and the time interval between adjacent QRS complexes).
The system of this invention provides means (tools, mechanisms) for the channel selection and control (adaptation) of the DSP operations described above. These control means include at least one of the following tools:
  user-controlled mechanical or electrical switches, adaptive software and firmware providing user-controlled adaptation parameters described above; and
  automatic adaptation of the DSP operations described above using programmable feedback/control software and firmware based on the EMI and cardiac waveform signals in different channels as described below.

Adaptive EMI Filtering

An important aspect of this invention is the selection of the channel for the detection of EMI spikes/peaks/artifacts (herein referred to as the "base-EMI channel"). Similar to the cardiac-activity-waveform tracking described below, the invention relies on the fact that the time of EMI peaks is the same in all channels. Therefore, the time points of occurrence of EMI peaks are determined in the base-EMI channel first. Subsequently, the same time points are used for tracking (and filtering EMI) in other channels.

The base-EMI channel is selected either by user (user-guided selection) or by the system (unguided selection) based on automatically determined EMI signal characteristics, such as the EMI-peak magnitude and/or signal-to-noise ratio (SNR).

When the times of occurrence of EMI peaks have been determined in the base-EMI channel, the EMI filtering is performed in other channels (physiological signals), using:
  a. the times of the EMI peaks in the base-EMI channel,
  b. the duration of the EMI-filtering time window (i.e., the time interval during which the EMI is removed from all filtered channels), which can be selected either by a user (user-guided selection) or by the system (unguided selection) based on the automatically determined EMI signal properties (characteristics) in various channels, such as the EMI-peak magnitude and duration, and
  c. the duration of the cardiac-activity-waveform-protection time window (herein referred to as the pivot window), during which EMI filtering is not performed in order to protect essential features of the cardiac-activity waveforms (e.g., ECG P, QRS, ST, and T waves) from filtering.
The EMI-detection and -filtering parameters, including the magnitude and derivative thresholds for detecting EMI peaks, duration of the EMI-filtering window, and the pivot window, are selected either by a user (user-guided selection) or by the system (unguided selection) based on the EMI signal properties, such as the magnitude and duration of EMI peaks and the time interval between them.

Tracking Cardiac-Activity Waveforms

The filtering and conditioning module identifies and tracks various forms of cardiovascular activity (e.g., ECG activity and its P, QRS, and T waves; ABP waveforms; and pulse oximetry waveforms). The DSP module also identifies and tracks EMI, e.g., GMF-generated spikes (peaks), whose frequency spectrum may overlap with the spectrum of QRS complexes. This overlap makes discrimination between the ECG QRS complexes (or other waveforms of cardiovascular activity) and GMF-generated EMI spikes technically challenging.

The filtering and conditioning module resolves this technical challenge by enabling selection of the channel (herein referred to as the "base channel") that is used for detection of cardiac-activity waveforms (e.g., ECG QRS complexes) and calculation of associated physiological parameters (e.g., heart rate or beat-to-beat intervals, duration of the QRS complexes and/or QT intervals). The base channel is selected either by a user (user-guided selection) or by the system (unguided selection) based on automatically determined cardiac-activity signal (waveform) characteristics, such as the magnitude of ECG R-waves and/or their SNR (where noise includes ambient noises and GMF-generated EMI).

The invention relies on the fact that the time of a specific type of cardiac activity (e.g., ECG activity and its QRS complex) is the same in all channels (i.e., in all ECG leads). Therefore, it is possible to select a base channel, in which cardiac activity (e.g., QRS complexes of high magnitude and high SNR) are readily identifiable and EMI is relatively small. Thereafter, this base channel is used for detection and tracking of cardiac activity (e.g., QRS complexes) and calculation of heart rate and other physiological parameter (beat-to-beat intervals, ST-segment amplitude, QT intervals, QRS duration, and T-wave amplitude). Once the time points of occurrence of the ECG QRS complexes have been determined in the base channel, the same time points are used for detecting QRS complexes in other channels. Some other examples of physiological signals that can also be detected and tracked using the base channel include ECG P waves and T waves, ABP waveforms, pulse oximetry waveforms, and other cardiovascular parameters.

The cardiac-waveform (e.g., ECG QRS complexes) detection parameters, including the magnitude and derivative thresholds, the QRS duration, and the time interval between adjacent QRS complexes, are selected either by a user (user-guided selection) or by the system (unguided selection) based on the properties of the cardiac waveforms, such as the magnitude and duration of ECG QRS complexes or other ECG waves, as well as their SNR. Averaging and other forms of low-pass filtering are used to improve the SNR.

The parameter selection may also include the properties of cardiac activity (e.g., the magnitude and duration of ECG QRS complexes or other ECG waves, the time interval between adjacent QRS complexes, as well as their SNR).

The filtering and conditioning module is implemented in a microcontroller (e.g., Texas Instruments, MSP-430), a microprocessor (e.g., Texas Instruments KEYSTONE, ARM CORTEX, C6000, Intel CORE i7 or ATOM, or an ATMEL ARM CORTEX processor), a field-programmable-gate-array (FPGA; e.g., Xilinx SPARTAN FPGA, Xilinx VIRTEX FPGA, or Altera Cyclone FPGA), a complex-programmable-logic device (CPLD), system-on-chip (SOC), or a general-purpose personal computer (PC).

Figure 26:
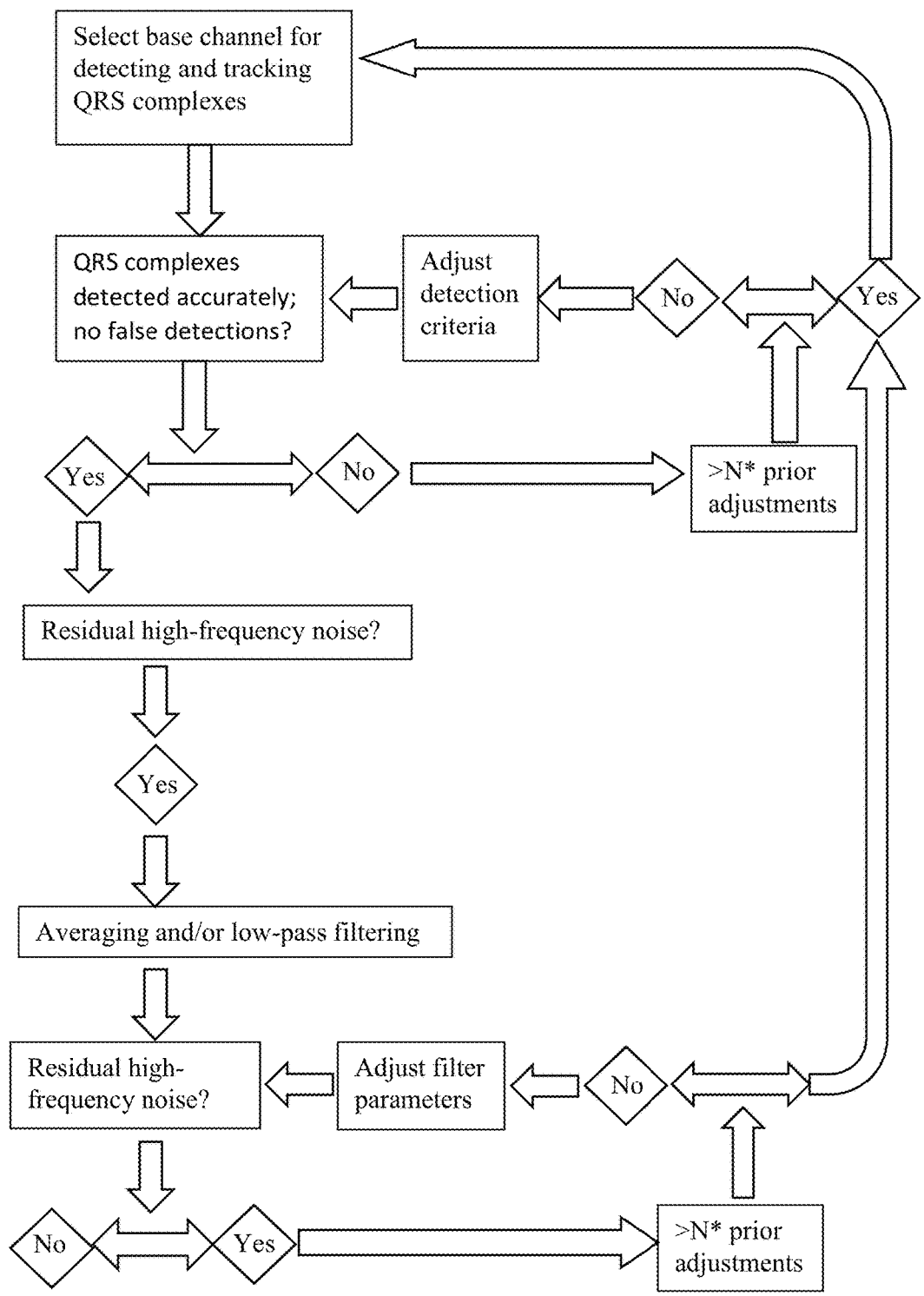
FIG. 26 is a flowchart of an adaptive DSP module performing tracking of cardiac activity (ECG QRS complexes).
Figure 27:
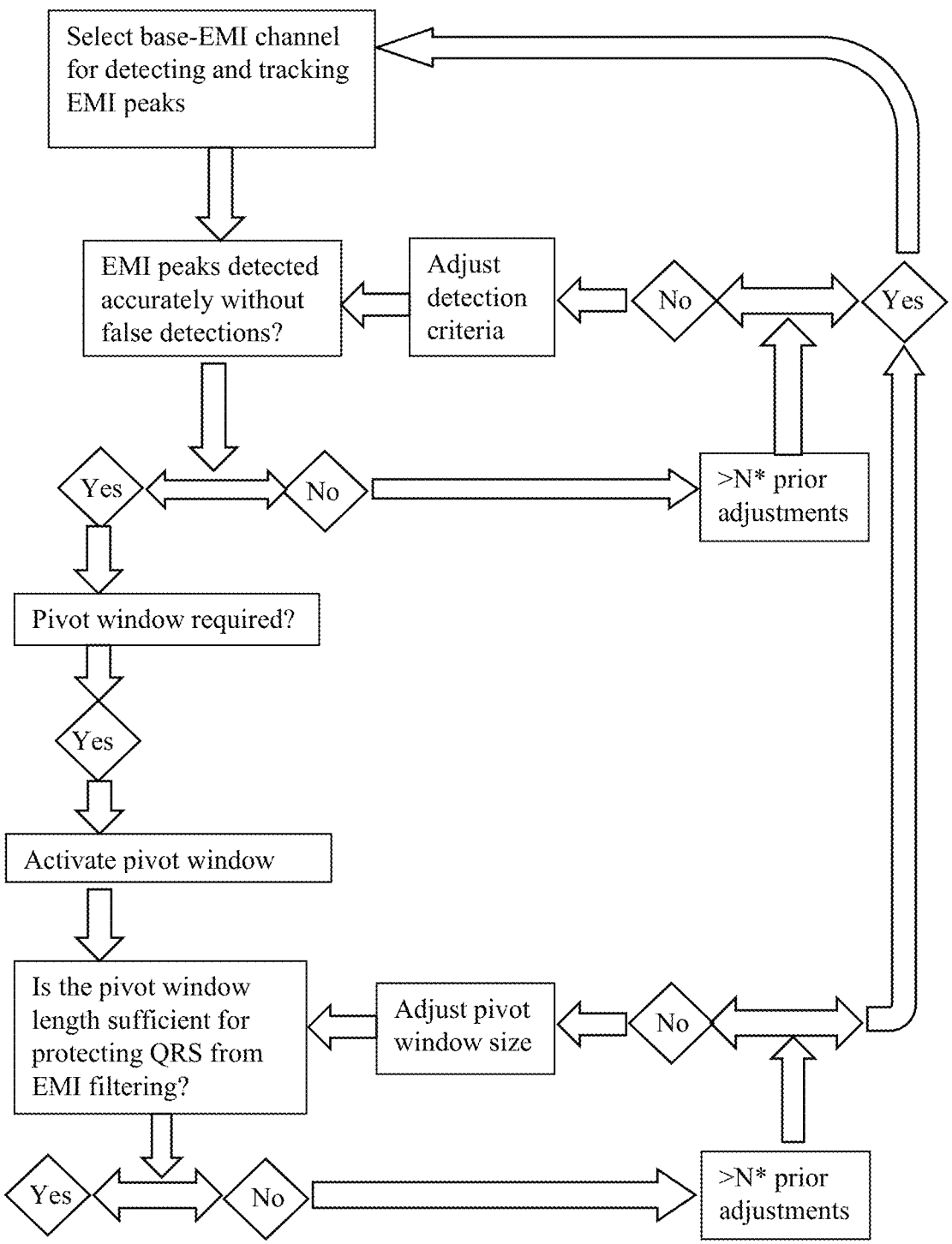
FIG. 27 is a flowchart of an adaptive DSP module performing EMI filtering.
Figure 28:
FIG. 28 shows an example of 12-lead ECG during real-time cardiovascular MR scanning (2-dimensional steady-state free precession, SSFP pulse sequence) with ~4 ms time-to-repeat (TR) and ~2 ms time-to-echo (TE). The EMI filtering is OFF. Note that the scanner produced GMF-generated high-frequency EMI spikes, which completely obscure ECG activity in most ECG leads.
Figure 29:
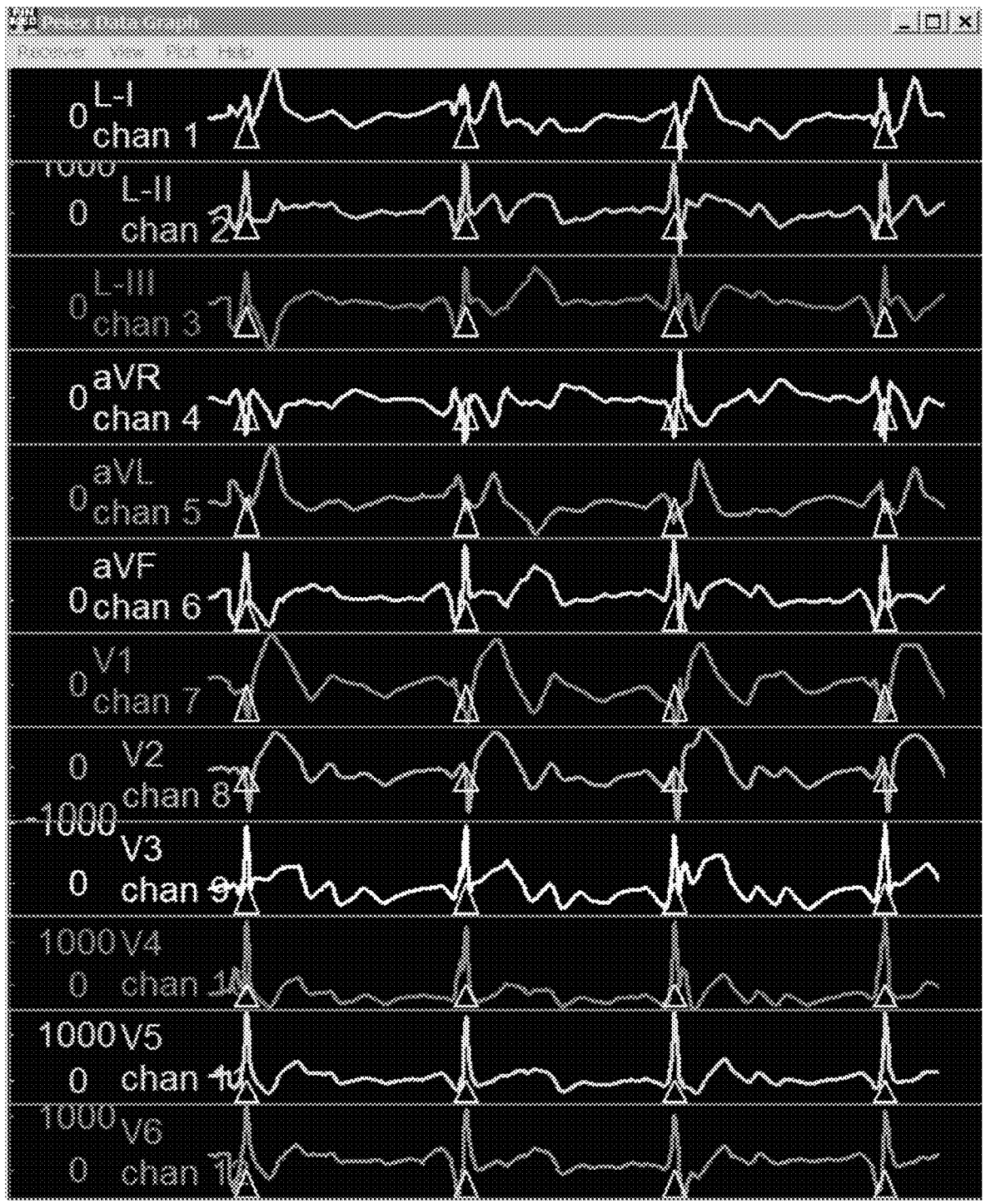
FIG. 29 shows the 12-lead ECG from FIG. 28 with the EMI filtering ON. The EMI filtering was performed using the following parameters: base EMI channel=10, EMI-peak amplitude: 0.5 of the total signal range, EMI-peak separation: 60, EMI-clearance window around the EMI peak: from −60 to 50 ms, base channel=10, QRS peak amplitude: 0.8 of the total range, peak-to-peak separation: 100 ms, pivot window around the QRS complex: from −30 to 40 ms. Note that the EMI spikes were successfully filtered from the ECG signals with minimal changes in the QRS complexes (which are marked by triangles).

FIG. 26 shows a flowchart of one embodiment of the adaptive DSP module performing tracking of cardiac activity (ECG QRS complexes). FIG. 27 shows a flowchart of one embodiment of the adaptive DSP module performing EMI filtering. FIG. 28 shows an example of 12-lead ECG recorded during cardiovascular MRI, using a 2D SSFP sequence with ultra-short duty cycle (TR ~4 ms, TE ~2 ms). Note that high-frequency EMI spikes completely obscure ECG QRS complexes when the EMI filtering is OFF. FIG. 29 shows the 12-lead ECG from FIG. 28 when the EMI filtering is ON. Note that the EMI spikes were filtered from the ECG signals with minimal distortion of the QRS complexes.

Example 1. Cardiovascular Magnetic-Resonance Imaging

Interventional MRI allows physicians to perform minimally invasive and catheter-based diagnostic procedures, providing high-quality images of internal organs, without exposure to harmful ionizing radiation. I-MM requires telemetry monitoring of patients' vital signs; however, existing telemetry monitors have electromagnetic compatibility (EMC) issues: MRI equipment is affected by electromagnetic interference (EMI) from telemetry systems, and telemetry data are degraded by the EMI generated by the MRI scanner. Commercial applications of the technology are expected to be in all areas of I-MRI. Because I-MRI enables physicians to perform minimally invasive procedures, eliminating the need for more invasive and traumatic procedures, its role in diagnostic evaluation is expected to grow rapidly.

As the field and applications of I-MM continue to grow and diversify, the need for wireless-telemetry monitoring of various physiological signals (multi-channel ECG, blood pressure and pulse oximetry) is also expected to follow. It is important, therefore, to develop a platform technology that is not limited to a small number of signals/channels, but has a sufficient number of channels and functions to be utilized for various future applications.

One particularly important emerging area of I-MRI is cardiovascular MR (CMR), which requires high-fidelity, real-time monitoring of multi-channel ECG for timely detection of life-threatening arrhythmias (which can be induced by cardiac catheterization) or the first signs of ischemic changes in the ST-segment. The latter is essential for the monitoring of patients with known or suspected coronary artery disease undergoing an exercise stress-CMR.

However, currently available ECG telemetry systems are limited to a few channels of non-diagnostic-quality ECG, which cannot provide accurate tracking of the ST-segment's amplitude and thus do not allow accurate and timely detection of potentially life-threatening ischemic events. Moreover, several telemetry units would be required for wireless monitoring of ECG, oxygen saturation and ABP, creating logistical difficulties for the medical personnel performing interventional MR procedures.

In this hypothetical example, an interventional CMR procedures is performed in a human subject, using a medical device of this invention. First, 10 ECG cables (for acquiring 12-lead ECG), two cables for monitoring blood pressure using fluid filled pressure cables, a cable for monitoring noninvasive blood pressure and an fiber-optical cable for monitoring pulse wave (pulse oximetry) are attached to the subject. The first set of signals is acquired outside the magnet bore providing an MHE-free reference data. The second set of signals is acquired after the patient is moved inside the magnet bore but before the scanning begins. This set of signals contains MHE but not GMF-interference. The third set of signals is acquired during the MR-scan, and this set contains both MHE and GMF-interference. Applying filtering and reconstructive procedures described in the Summary of Invention, diagnostic physiological signals are reconstructed from those obtained during MR-scan.

Because the number of channels and their sampling rate are relatively high, the data are transmitted in two parallel data streams using two wireless transmitters. The first transmitter transmits 8 ECG channels, whereas the second transmits blood pressure and pulse oximetry channels. The data are time-stamped using time markers (periodic impulses) that are recorded using a dedicated reference channel in each data stream. These time markers are used by the receiving station to synchronize the two data streams by time-aligning the corresponding time markers.

The interventional CMR procedures often require X-ray imaging as well. For this purpose, patient table is quickly moved to an adjacent X-ray imaging room. Because a medical device of this invention is wireless, it does not restrict movement of the patient table and provides uninterrupted monitoring during the patient transportation from the MR-room to X-ray room. To provide diagnostic quality monitoring during X-ray (fluoroscopy) guided procedure (which does not have a high-level GMF), Filterbank II is switched to Filterbank I.

Example 2. MRI-Guided Cardiac Electrophysiology Study

This hypothetical example describes application of a medical device of this invention for the MR-guided cardiac electrophysiology imaging. The monitoring procedure is similar to that described in example 1. However, the system configuration required for this time-critical setting is different. First, the system uses two parallel data streams passed through both Filterbanks I and II, to allow clinicians monitor interchangeably or concurrently signals passed through both filterbanks. Second, all data channels are transmitted at two different frequencies (2.4 and 5.2 GHz), using two wireless transmitters, to ensure uninterrupted transmission of all data channels in this time-critical setting. This redundant transmission ensures that the receiving station receives all the data channels if one transmission frequency becomes unavailable or experiences a transmission delay.

Example 3. Magnetic-Resonance Imaging of the Brain

This hypothetical example describes application of a medical device of this invention for high-resolution brain imaging requires data recording from up to 100 channels simultaneously, at a high sampling frequency. The monitoring and setup procedures are similar to those described in examples 1 and 2. However, because the number of monitoring channels is bigger, the system configuration is expanded to include ten data acquisition modules with associated wireless transmitters, which are time-synchronized as described above.

Whereas particular aspects of the method of the present invention and particular embodiments of the invention have been described for purposes of illustration, it will be appreciated by those skilled in the art that numerous variations of the details may be made without departing from the invention as described in the appended claims.

The invention claimed is:

1. A wireless system for monitoring health data of an individual lying on a movable patient table, said system including:
at least one acquisition module with at least one sensor adapted to be placed on an individual's skin for collecting at least one physiological signal by substantially continuous monitoring of said individual's health data regardless of movement of said patient table and movement of medical personnel around said table, and at least one wireless transmitter for substantially continuous transmission of said at least one physiological signal;
wherein said at least one wireless transmitter includes at least one first antenna linked to said patient table to receive said at least one physiological signal from said acquisition module and transmit said signal from said individual on said movable patient table;
wherein said at least one first antenna is positioned to provide substantially unobstructed communication to at least one second antenna on a receiver regardless of the location of said patient table and the movement of medical personnel around said table; and
at least one EMI filtering and conditioning module with at least one filtering and detection parameter based on the properties of EMI wherein said filtering and detection parameter is selected from at least one data channel (signal) used for detecting EMI, at least one data channel used for detecting cardiac-activity waveforms, at least one time window for disabling EMI filtering to protect essential features of the cardiac-activity waveforms, at least one EMI-clearance window around the EMI peak, at least one time window for EMI filtering, EMI magnitude, at least one EMI derivative, and at least one time window between the EMI peaks.

2. A system as set forth in claim 1 in which said at least one first antenna extends to at least six feet above the floor to provide substantially unobstructed communication with said at least one second antenna.

3. A system as set forth in claim 1 in which said at least one first antenna is located below the patient level to provide substantially unobstructed communication between said first antenna and said at least one second antenna located on the floor surface.

4. A system as set forth in claim 3 in which said at least one first antenna includes a metal frame in said patient table.

5. A system as set forth in claim 1 in which said at least one first antenna is mounted on at least one pole selected from a table-mounted pole and a freestanding pole.

6. A system as set forth in claim 1 in which said at least one first antenna is mounted inside at least one pole selected from a table-mounted pole and a freestanding pole.

7. A system as set forth in claim 1 in which said at least one first antenna includes at least one pole selected from a table-mounted pole and a freestanding pole.

8. A system as set forth in claim 1 in which said wireless transmitter includes at least one of Bluetooth, WiFi, ZigBee, infrared, and other types of wireless transmitters.

9. A wireless system for monitoring health data of an individual, said system including:
at least one acquisition module with at least one sensor adapted to be placed on the skin of an individual lying on a movable table for collecting at least one physiological signal by substantially continuous monitoring of said individual's health data;
at least one wireless transmitter for substantially continuous transmission of said data with said transmitter having at least one first antenna linked to said movable table to receive said at least one physiological signal from said acquisition module and transmit said signal from said individual on said movable patient table;
at least one wireless receiver having at least one second antenna for receiving said data substantially continuously from said wireless transmitter; and
at least one EMI filtering and conditioning module with adaptation of at least one filtering and detection parameter based on the properties of EMI, wherein said filtering and detection parameter is selected from at least one data channel (signal) for detecting EMI, at least one data channel for detecting cardiac-activity waveforms, at least one time window for EMI filtering, at least one pivot time window for disabling EMI filtering to protect essential features of the cardiac-activity waveforms, and at least one EMI-detection parameters, including EMI magnitude, derivative, and time window between the EMI peaks.

10. A wireless system as set forth in claim 9, which includes at least one manual control for user guidance of said at least one filtering and detection parameter.

11. A wireless system as set forth in claim 9, which includes at least one processing element that substantially continuously receives information about EMI and automatically adapts at least one parameter for EMI filtering and cardiac-activity waveform tracking.

12. A wireless system as set forth in claim 1, which includes at least one EMI filtering and conditioning module with adaptation of at least one filtering and detection parameter based on the properties of EMI, wherein said filtering and detection parameter is selected from: channel selection for detecting EMI, channel selection for detecting cardiac-activity waveforms, time window selection for EMI filtering, selection of a pivot time window for disabling EMI filtering to protect essential features of the cardiac-activity waveforms, and EMI-detection parameters, including EMI magnitude, derivative, and time window between the EMI peaks.

13. A wireless system as set forth in claim 12, which includes at least one manual control for user guidance of said at least one filtering and detection parameter.

14. A wireless system as set forth in claim 12, which includes at least one automatically adapted parameter for EMI filtering and cardiac-activity waveform tracking.

15. A method for monitoring health data of an individual lying on a movable patient table, comprising substantially continuously collecting said health data from an individual, wirelessly transmitting said data using a first antenna to a receiver having a second antenna, and filtering said health data using at least one adaptation of the EMI filtering and cardiac-waveform tracking based on the properties of EMI, wherein said adaptation is selected from: channel selection for detecting EMI, channel selection for detecting cardiac-activity waveforms, time window selection for EMI filtering, selection of a pivot time window for disabling EMI filtering to protect essential features of the cardiac-activity waveforms, and EMI-detection parameters, including at least one parameter selected from EMI magnitude, EMI derivative, and time window between the EMI peaks.

16. A method as set forth in claim 15 in which said at least one adaptation is performed using at least one channel selected from a user-determined channel and a system-determined channel.

* * * * *